US012616568B2

(12) United States Patent
Von Oepen et al.

(10) Patent No.: US 12,616,568 B2
(45) Date of Patent: May 5, 2026

(54) TWO STAGE TRICUSPID VALVE IMPLANT

(71) Applicant: St. Jude Medical, Cardiology Division, Inc., St. Paul, MN (US)

(72) Inventors: Randolf Von Oepen, Aptos, CA (US); Grayston Licht, Riverside, CA (US); Preston James Huddleston, Maplewood, MN (US); Son Mai, North Branch, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 666 days.

(21) Appl. No.: 18/067,993

(22) Filed: Dec. 19, 2022

(65) Prior Publication Data

US 2023/0277304 A1 Sep. 7, 2023

Related U.S. Application Data

(60) Provisional application No. 63/315,144, filed on Mar. 1, 2022.

(51) Int. Cl.
*A61F 2/24* (2006.01)

(52) U.S. Cl.
CPC .... *A61F 2/2409* (2013.01); *A61F 2210/0014* (2013.01); *A61F 2230/0021* (2013.01); *A61F 2230/0039* (2013.01); *A61F 2230/0078* (2013.01); *A61F 2250/0018* (2013.01); *A61F 2250/0063* (2013.01)

(58) Field of Classification Search
CPC ...................................................... A61F 2/24
See application file for complete search history.

(56) References Cited

U.S. PATENT DOCUMENTS

| | | | | |
|---|---|---|---|---|
| 8,845,722 B2 * | 9/2014 | Gabbay | ................. | A61F 2/2409 |
| | | | | 623/2.14 |
| 10,105,224 B2 * | 10/2018 | Buchbinder | .......... | A61F 2/2409 |
| 10,548,722 B2 | 2/2020 | Morin | | |
| 10,905,550 B2 * | 2/2021 | Lally | ..................... | A61F 2/2436 |
| 11,707,355 B2 * | 7/2023 | McVeigh | .............. | A61F 2/2436 |
| | | | | 623/2.17 |
| 2010/0082094 A1 * | 4/2010 | Quadri | .................. | A61F 2/2412 |
| | | | | 29/890.132 |

(Continued)

FOREIGN PATENT DOCUMENTS

EP           3915523 A1    12/2021

*Primary Examiner* — Jacqueline Woznicki
(74) *Attorney, Agent, or Firm* — SLEMAN & LUND LLP

(57) ABSTRACT

A prosthetic tricuspid heart valve system includes a collapsible anchor frame and a collapsible prosthetic heart valve. The anchor includes a support structure having a waisted central portion, and atrial and ventricular flared portions sized to clamp a native valve annulus. Atrial and ventricular sheets are coupled to the atrial and ventricular flared portions, and each include a central aperture. A generally cylindrical fabric valve-receiving member has an inflow end coupled to the atrial sheet and an outflow end coupled to the ventricular sheet to provide a conduit through the valve-receiving member between the atrial and ventricular sheet. The prosthetic heart valve may include a stent and a plurality of prosthetic leaflets, the prosthetic heart valve configured to be expanded into and received within the valve-receiving member of the anchor frame.

20 Claims, 21 Drawing Sheets

(56)          References Cited

U.S. PATENT DOCUMENTS

| | | | |
|---|---|---|---|
| 2010/0217382 A1* | 8/2010 | Chau | A61F 2/2457 |
| | | | 623/2.12 |
| 2011/0029072 A1* | 2/2011 | Gabbay | A61F 2/2418 |
| | | | 623/2.37 |
| 2012/0059458 A1* | 3/2012 | Buchbinder | A61F 2/2409 |
| | | | 623/2.36 |
| 2014/0005778 A1 | 1/2014 | Buchbinder | |
| 2014/0228945 A1* | 8/2014 | Valdez | A61F 2/2412 |
| | | | 623/2.18 |
| 2014/0324164 A1* | 10/2014 | Gross | A61F 2/2418 |
| | | | 623/2.37 |
| 2014/0350669 A1* | 11/2014 | Gillespie | A61F 2/2442 |
| | | | 623/2.18 |
| 2015/0272737 A1* | 10/2015 | Dale | A61F 2/2418 |
| | | | 623/2.37 |
| 2015/0327999 A1* | 11/2015 | Board | A61F 2/2427 |
| | | | 623/2.11 |
| 2016/0324633 A1 | 11/2016 | Gross | |
| 2016/0361161 A1* | 12/2016 | Braido | A61F 2/2409 |
| 2017/0165065 A1* | 6/2017 | Rothstein | A61F 2/2439 |
| 2018/0055629 A1* | 3/2018 | Oba | A61F 2/2409 |
| 2018/0296341 A1 | 10/2018 | Noe | |
| 2020/0000579 A1* | 1/2020 | Manash | A61F 2/2412 |
| 2020/0188100 A1* | 6/2020 | Vidlund | A61F 2/2418 |
| 2021/0228349 A1* | 7/2021 | Vidlund | A61F 2/2457 |
| 2022/0023037 A1 | 1/2022 | Moore | |
| 2022/0087814 A1* | 3/2022 | Vidlund | A61F 2/2418 |
| 2022/0192824 A1 | 6/2022 | Vidlund | |
| 2023/0277307 A1* | 9/2023 | Noe | A61F 2/2439 |
| | | | 623/2.18 |
| 2023/0397985 A1* | 12/2023 | Von Oepen | A61F 2/2418 |
| 2024/0091000 A1* | 3/2024 | King | A61F 2/2418 |
| 2024/0108459 A1* | 4/2024 | Dinh | A61F 2/2409 |

* cited by examiner

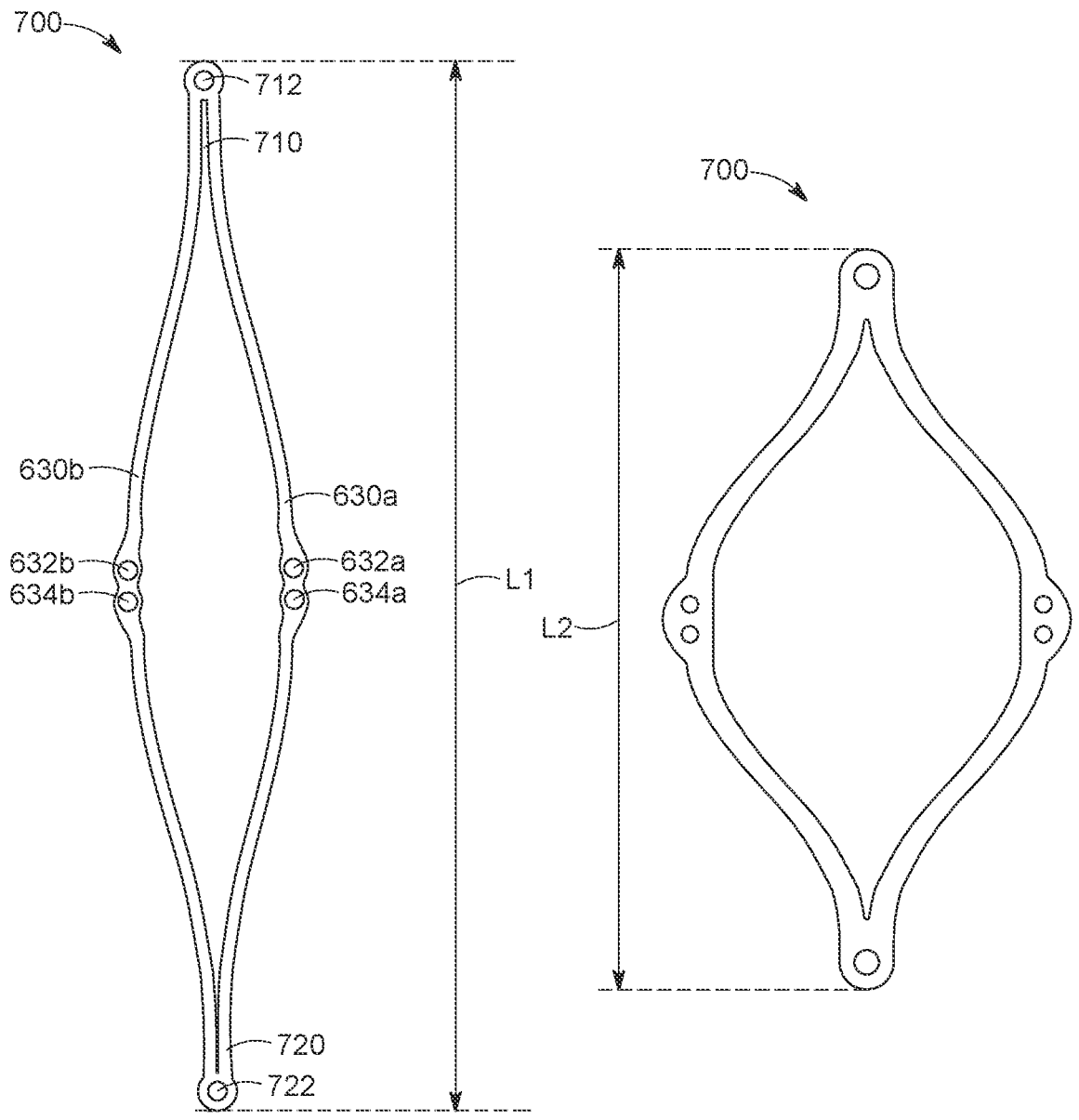
FIG. 10A                    FIG. 10B

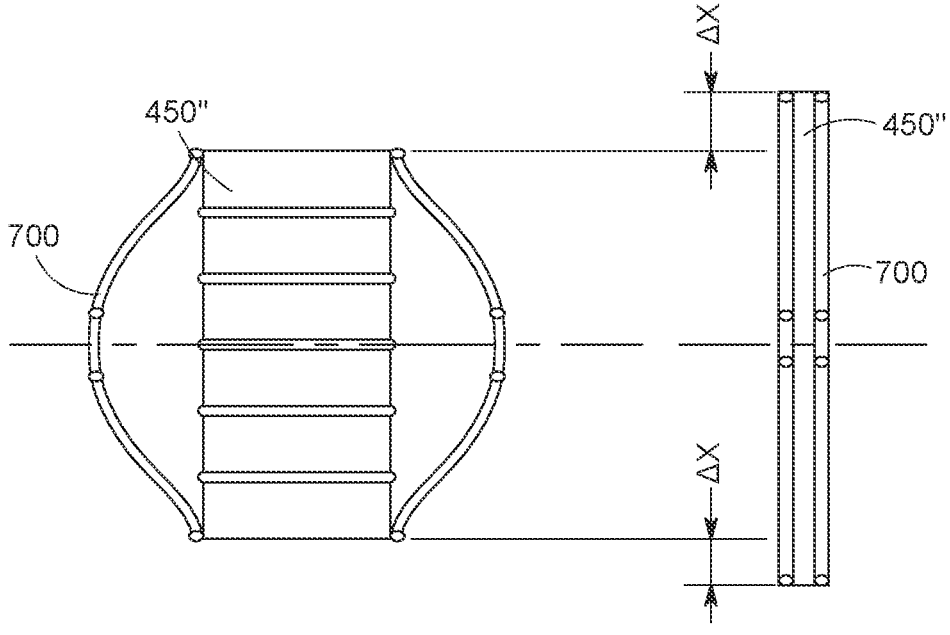
FIG. 10E                    FIG. 10F

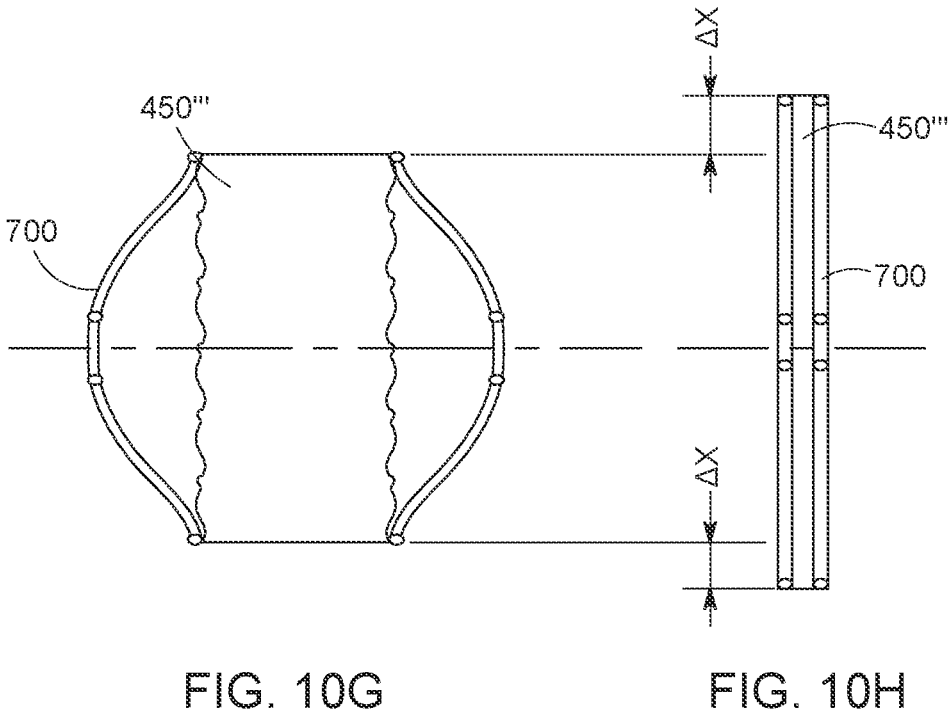
FIG. 10G                    FIG. 10H

TWO STAGE TRICUSPID VALVE IMPLANT

CROSS-REFERENCE TO RELATED APPLICATIONS

This application claims priority to the filing date of U.S. Provisional Patent Application No. 63/315,144, filed Mar. 1, 2022, the disclosure of which is hereby incorporated by reference herein.

BACKGROUND OF THE DISCLOSURE

The heart has four native valves, including the aortic valve, pulmonary valve, mitral valve (also known as the left atrioventricular valve) and the tricuspid valve (also known as the right atrioventricular valve). When these valves begin to fail, for example by not fully coapting and allowing retrograde blood flow (or regurgitation) across the valve, it may be desirable to repair or replace the valve. Prosthetic replacement heart valves may be surgically implanted via an open chest, open heart procedure while the patient is on cardiopulmonary bypass. However, such procedures are extremely invasive and frail patients, who may be the most likely to be in need of a prosthetic heart valve, may not be likely to survive such a procedure. More recently, prosthetic heart valves have been trending to less invasive procedures, including collapsible and expandable heart valves that can be delivered through the vasculature in a transcatheter procedure.

Unless otherwise indicated, as used herein, the term "tricuspid valve" refers to the right atrioventricular valve, as opposed to just a generic term for a three-leaflet valve. Initial human trials to replace the native tricuspid valve in a transcatheter procedure (e.g. via the femoral vein) have shown promising results, with patients experience significant improvements in quality of life after the prosthetic valve implantation. It is thought that important characteristics of a successful transcatheter prosthetic tricuspid valve device includes not only a good clinical outcome for the patient, but ease of use of the tricuspid valve, including for example having a small enough size to be able to avoid a surgical cut down of the patient's femoral vein for delivery.

BRIEF SUMMARY OF THE DISCLOSURE

According to one aspect of the disclosure, a prosthetic heart valve system for replacing a native right atrioventricular valve may include a collapsible and expandable anchor frame and a collapsible and expandable prosthetic heart valve. The anchor may include a support structure that, in an expanded condition, has a waisted central portion, and atrial and ventricular portions each flared radially outwardly from the central portion. The atrial and ventricular portions may be sized to clamp an annulus of the right atrioventricular valve therebetween. It should be understood that, as used herein, the term "clamp" does not require an active mechanical action, but includes sandwiching and similar concepts. An atrial sheet may be coupled to the atrial portion of the support structure and may extend radially inwardly to a central aperture in the atrial sheet. A ventricular sheet may be coupled to the ventricular portion of the support structure and may extending radially inwardly to a central aperture in the ventricular sheet. A valve-receiving member may be formed of fabric and may be generally cylindrical. An inflow end of the valve-receiving member may be coupled to the atrial sheet and an outflow end of the valve-receiving member may be coupled to the ventricular sheet to provide a conduit from the central aperture in the atrial sheet to the central aperture in the ventricular sheet through the valve-receiving member. The prosthetic heart valve may include a stent and a plurality of prosthetic leaflets, the prosthetic heart valve configured to be expanded into and received within the valve-receiving member of the anchor frame.

Another aspect of the disclosure involves a method of replacing a native right atrioventricular valve of a patient. The method includes delivering a collapsible and expandable anchor frame to the native right atrioventricular valve while the anchor frame is in a collapsed condition within a first delivery sheath. The anchor frame is deployed from the delivery sheath, and the anchor frame is expanded within the native right atrioventricular valve so that an annulus of the native right atrioventricular valve is clamped between an atrial portion of the anchor frame and a ventricular portion of the anchor frame. After deploying the anchor frame, blood is allowed to flow through a conduit of the anchor frame. The conduit is formed by a fabric valve-receiving member that has an inflow end and an outflow end. The inflow end of the valve-receiving member is coupled to an atrial sheet that is coupled to the atrial portion of the anchor frame. The outflow end of the valve-receiving member is coupled to a ventricular sheet that is coupled to the ventricular portion of the anchor frame. After allowing blood to flow through the conduit of the anchor frame, a collapsible and expandable prosthetic heart valve is delivered to the anchor frame. The prosthetic heart valve is expanded into contact with the valve-receiving member, the valve-receiving member maintaining the prosthetic heart valve within the native right atrioventricular valve.

3

Figures 10C, 10D:
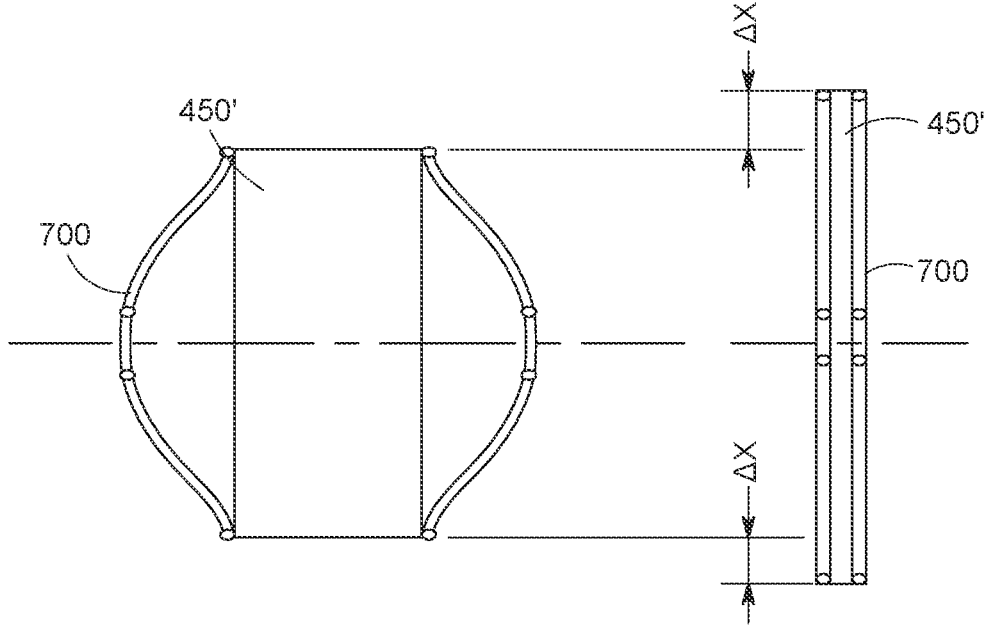
FIG. 10A is a front view of a support arm for use with an anchor frame according to another embodiment of the disclosure, with the support arm being shown in a partially expanded condition.
FIG. 10B is a front view the support arm of FIG. 10A in an expanded condition.

FIG. 10C is a side view of a plurality of the support arms of FIG. 10A coupled to a valve-receiving member, according to another aspect of the disclosure, in an expanded condition.

FIG. 10D is a side view of the configuration of FIG. 10C in a collapsed condition.

FIG. 10E is a side view of a plurality of the support arms of FIG. 10A coupled to a valve-receiving member, according to further aspect of the disclosure, in an expanded condition.

FIG. 10F is a side view of the configuration of FIG. 10E in a collapsed condition.

FIG. 10G is a side view of a plurality of the support arms of FIG. 10A coupled to a valve-receiving member, according to still another aspect of the disclosure, in an expanded condition.

FIG. 10H is a side view of the configuration of FIG. 10G in a collapsed condition.

Figure 6:
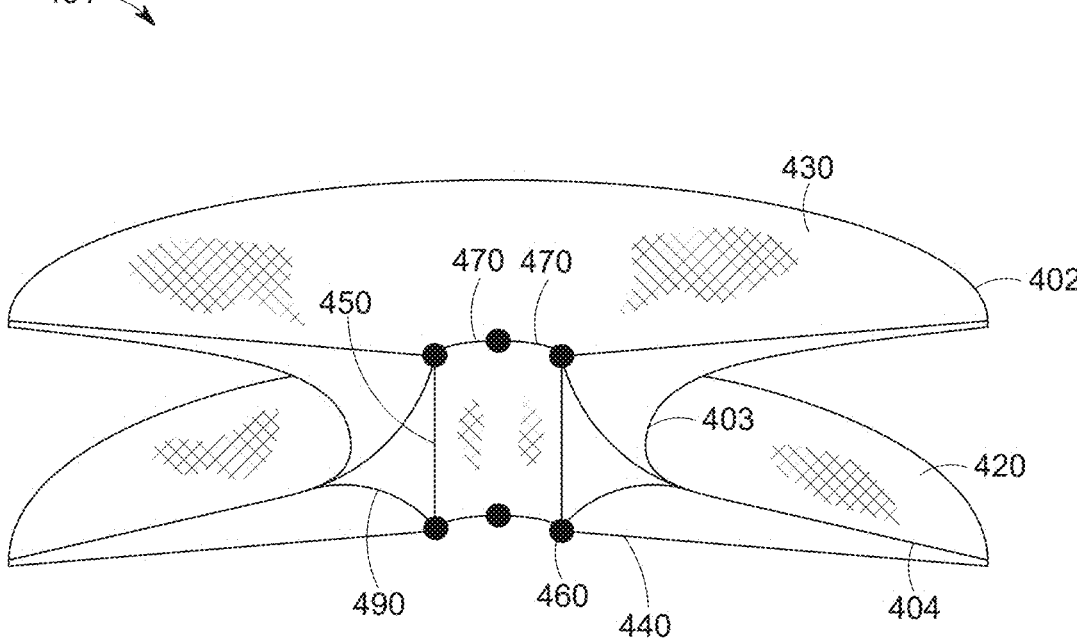
FIG. 6 is a cross-section of an anchor frame according to another aspect of the disclosure.
Figure 11:
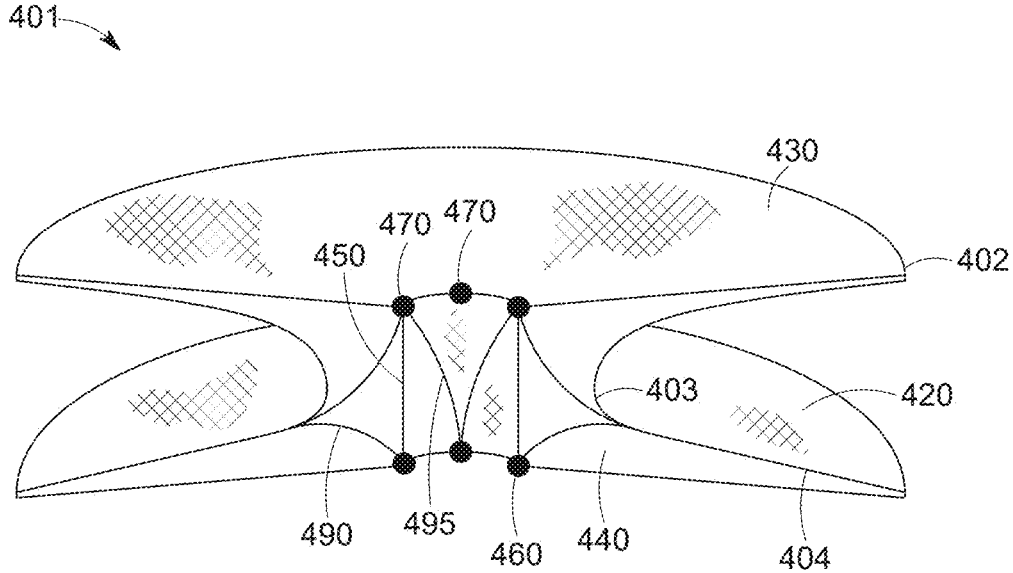

FIG. 11 is a cross-section of the anchor frame of FIG. 6 with a plurality of leaflets coupled to the valve-receiving member of the anchor frame.

Figure 12:
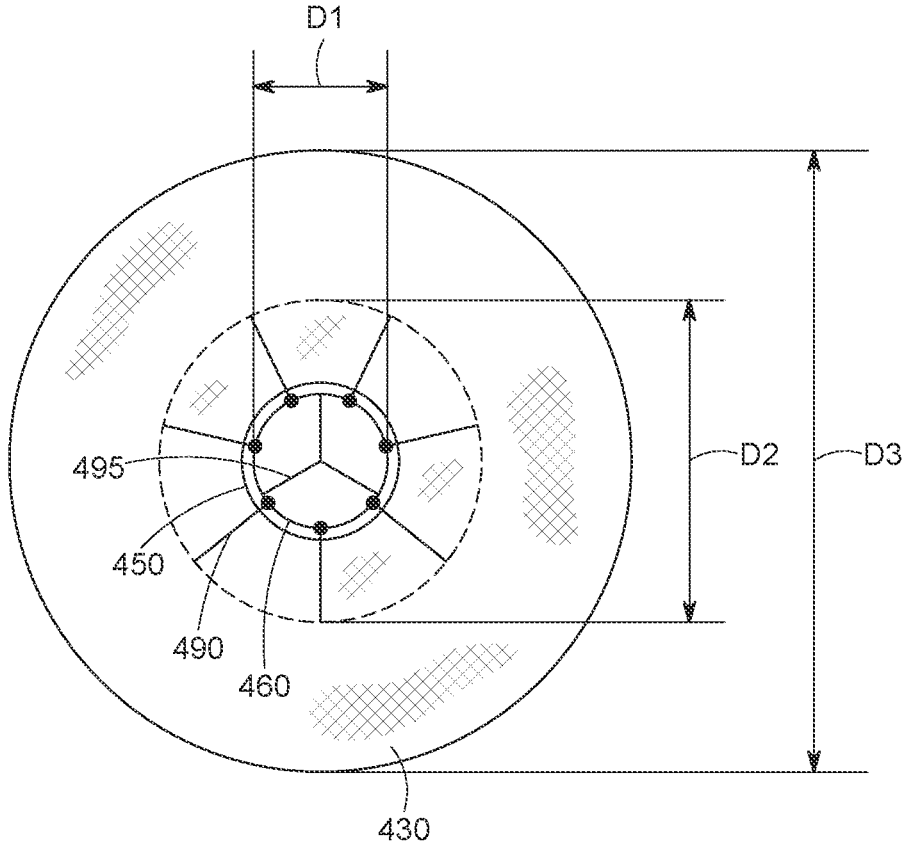

FIG. 12 is a top view of the anchor frame of FIG. 11.

Figure 3:
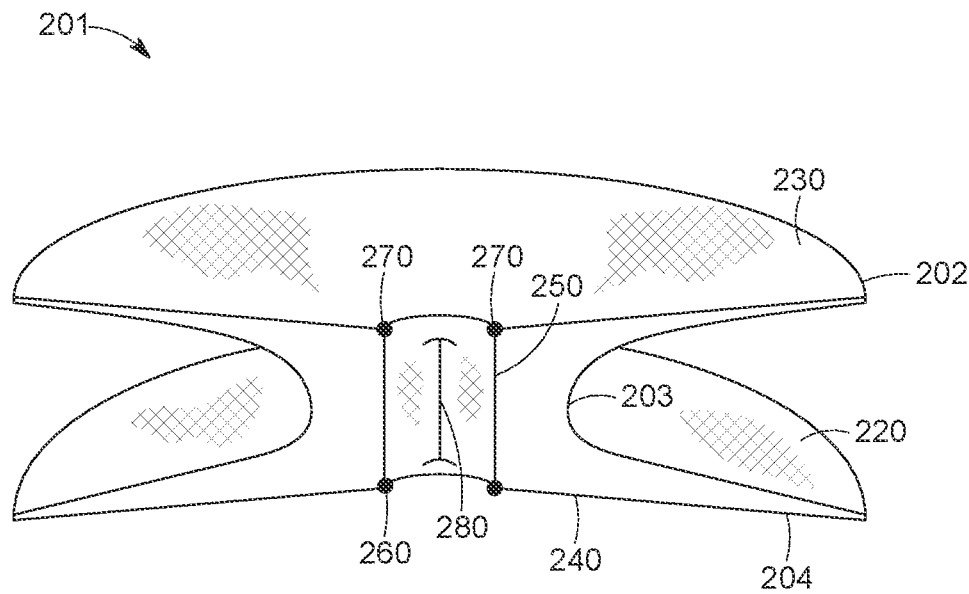
FIG. 3 is a cross-section of an anchor frame according to one aspect of the disclosure.
Figure 13A:
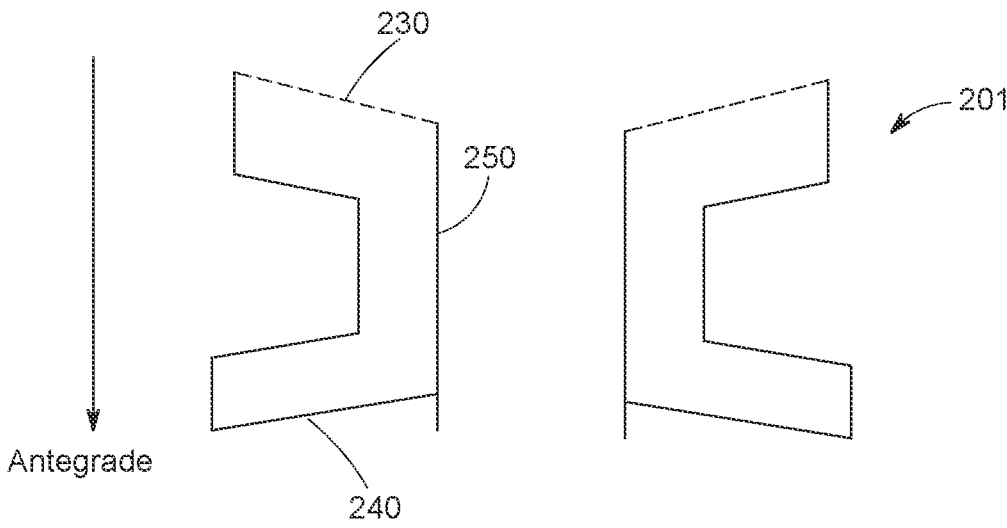
Figure 13B:
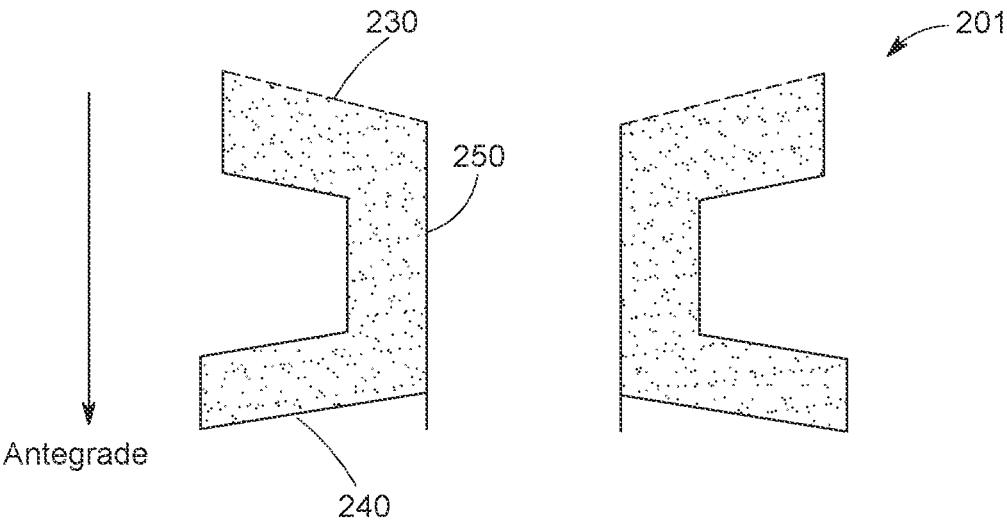

FIGS. 13A-B are schematic views of the anchor frame of FIG. 3 before and after, respectively, blood has coagulated between the atrial and ventricular sheets.

Figure 14A:
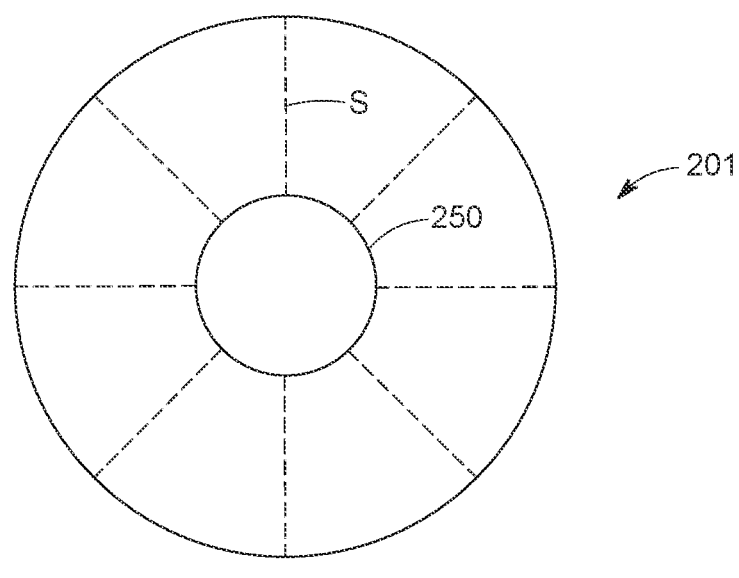
Figure 14B:
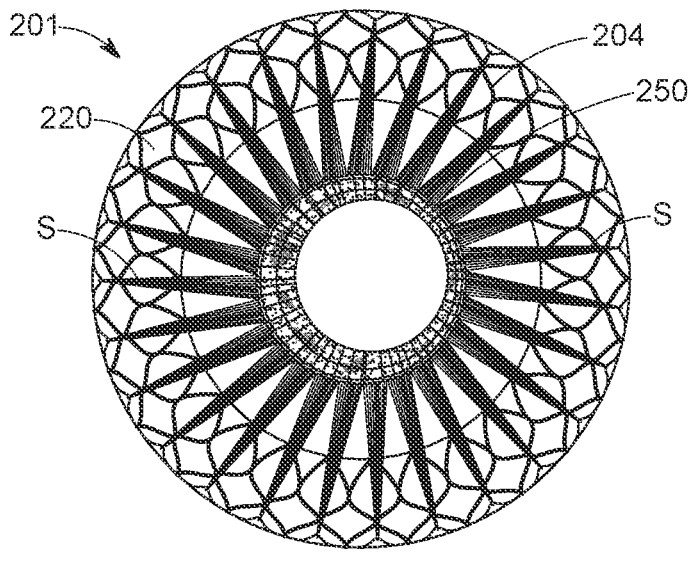

FIGS. 14A-B are views of the valve-receiving member being suspended within the anchor frame of FIG. 3 via radially extending sutures.

Figure 15A:
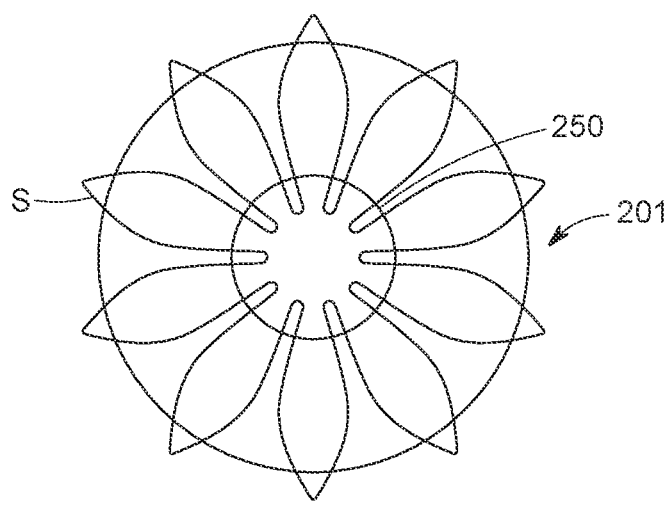
Figure 15B:
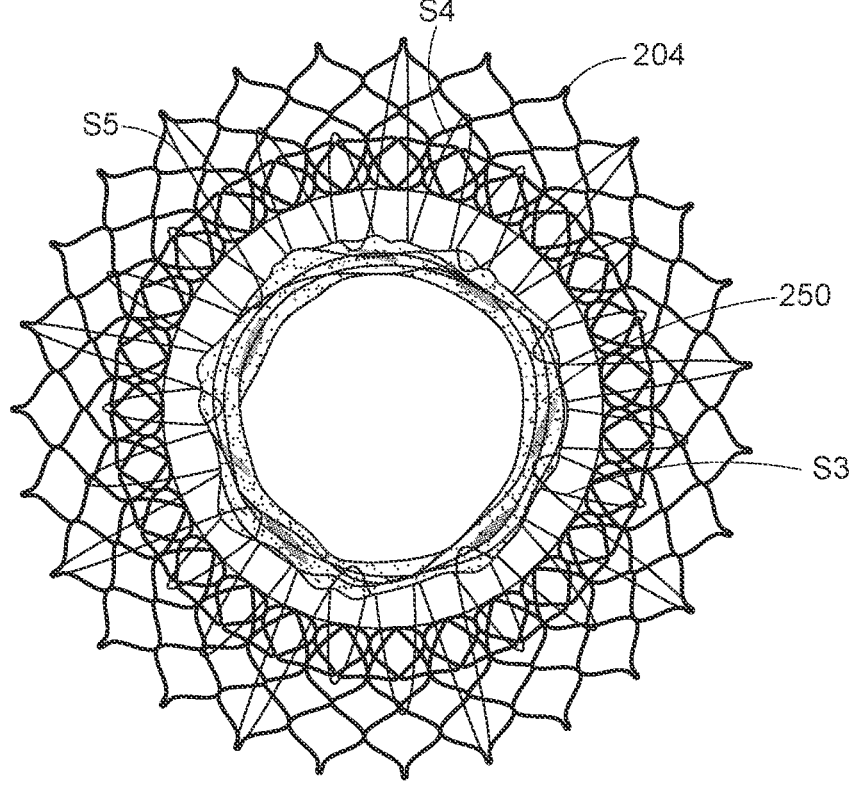
Figure 15C:
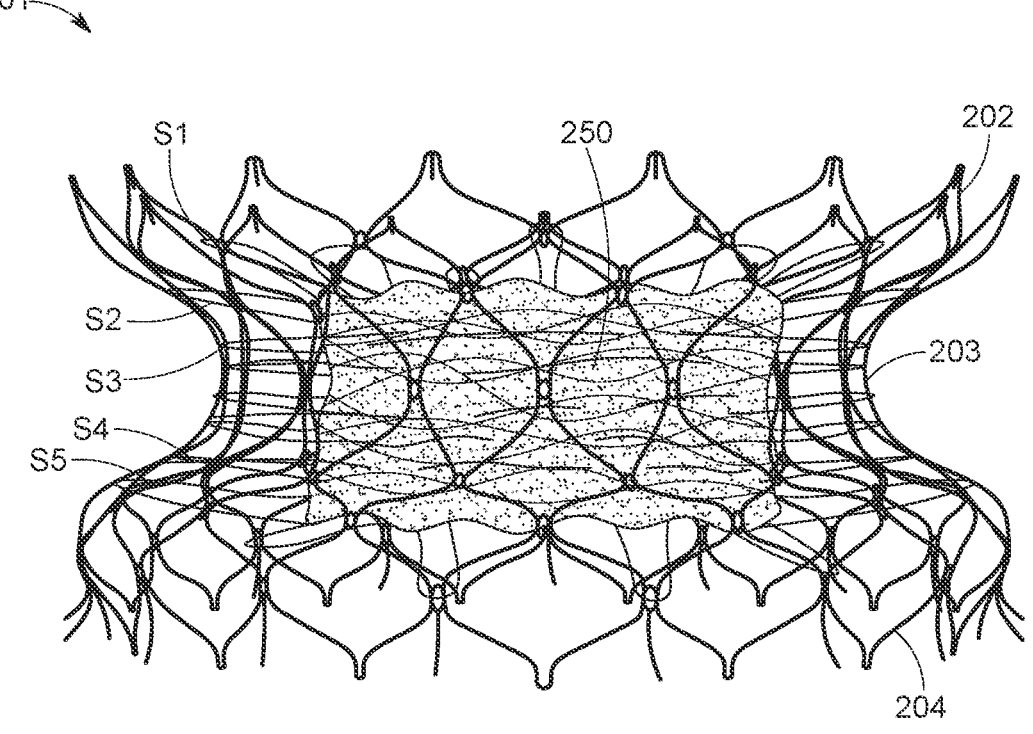

FIGS. 15A-C are views of the valve-receiving member being suspended within the anchor frame of FIG. 3 via continuous, circumferentially extending suture loops.

DETAILED DESCRIPTION OF THE DISCLOSURE

Figure 1:
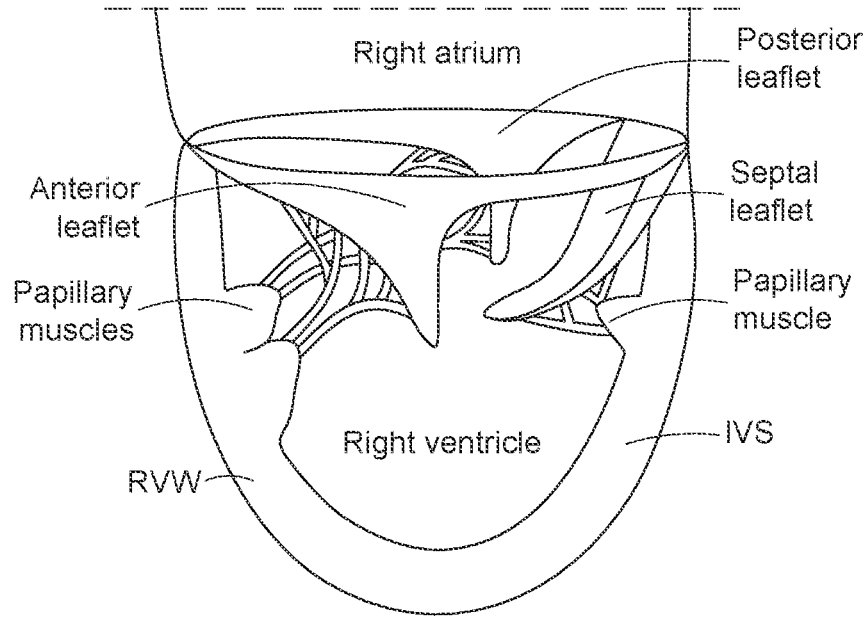
FIG. 1 is a schematic illustration of the right atrioventricular valve.

FIG. 1 is a schematic illustration of the right atrioventricular valve (commonly referred to as the tricuspid valve). The tricuspid valve separates the right atrium from the right ventricle, and typically includes three leaflets, including a posterior leaflet, an anterior leaflet, and a septal leaflet. The septal leaflet is positioned nearest the interventricular septum ("IVS"). The tricuspid valve annulus may include conduction nodes near the connection point between the annulus and the septal leaflet, including for example atrioventricular node ("AV node"). Electrical impulses may be conducted from the AV node, via the bundle of His, to the Purkinje fibers that provide electrical conduction to the ventricles. Papillary muscles along the right ventricular wall ("RVW") may support chordae tendineae coupled to the tricuspid valve leaflets to prevent inversion of the leaflets during normal physiological operation. The left atrioventricular valve (commonly referred to as the mitral valve) may have a generally similar structure as the tricuspid valve, although many differences do exist—including for example mitral valve typically includes two leaflets (an anterior and posterior leaflet) and has the general shape of a hyperbolic paraboloid or "saddle"-type shape. Both the mitral valve annulus and tricuspid valve annulus may be very large compared to the aortic and pulmonary valves. For example, the tricuspid valve may have a diameter of between 45-50 mm in a patient with moderate tricuspid valve disease, and a diameter of between 50-60 mm in a patient with severe tricuspid valve disease. Diameters of up to 67 mm have been encountered in disease tricuspid valves, although even larger sized annuluses may be encountered.

Despite the tricuspid valve typically having three leaflets, the reality is that the number of leaflets in any given patient, and particularly in patients with tricuspid valve problems such as severe or torrential regurgitation, is unpredictable, and it may not be uncommon for a given patient to have anywhere between two leaflets and eight (or even more) leaflets. One result of this unpredictability is that prosthetic tricuspid heart valves that rely on anchoring to the native tricuspid valve leaflets may encounter difficulties. For example, at least one transcatheter prosthetic tricuspid valve includes a plurality of "arms" that are intended to hook around the native tricuspid valve leaflets in order to properly position and anchor the prosthesis within the native tricuspid valve annulus. Visualization (e.g. via echocardiography) of the native tricuspid valve leaflets for these patients, including to confirm the desired positioning and anchoring of a prosthetic tricuspid valve with anchoring "arms," can be extremely difficult. And even though the term "arms" is used above, visualization to confirm leaflet anchoring by other mechanisms (e.g. clips or pinching the leaflets) may be similarly difficult. This difficulty may lead to a relatively long procedure time, and less-than-optimal positioning and anchoring of this type of prosthetic tricuspid valve. As should be understood, achieving good positioning and anchoring of a prosthetic tricuspid valve within the native tricuspid valve is one important aspect of achieving good patient results with prosthetic tricuspid valves. The ease of use and length of procedures is a related parameter that is important for both good patient results and successful adoption by physicians. Thus, it would be desirable for a transcatheter prosthetic tricuspid valve to be able to achieve good anchoring, preferably without significant reliance on imaging to achieve that anchoring.

Another important aspect of transcatheter tricuspid valve implantations is the size of components introduced into the patient's body. For example, it may be preferable for the delivery device that is used to deliver the transcatheter tricuspid valve to be small enough to be delivered through the femoral vein without requiring surgical cut down of the vein. One desirable size example is about 30 French (10 mm) or below. Further, given the requirement for a transcatheter valve to be delivered through the patient's vasculature, the components of the system must be small enough to pass through the patient's vasculature safely. This size objective may be, in some respect, at odds with the anchoring objective. In other words, the inclusion of a relatively large amount of anchoring structures in a prosthetic tricuspid valve may help provide better anchoring, but at a cost of increasing the overall size of the device (and thus the components, such as a delivery device, that will house the prosthetic heart valve).

Although the size objective may sometimes be at odds with the anchoring objective, prosthetic tricuspid valves are described herein that solve this problem, at least in part, by the use of a two-part prosthetic heart valve system which includes an anchoring component that can be delivered separately from the valve component. For example, by allowing delivery and deployment of an anchoring component at a first time, and then delivery and deployment of the valve component at a second time later than the first time, the two components do not "stack" on each other while housed within the delivery device, allowing for a smaller size delivery device compared to a system in which the anchoring and valve components are coupled together during delivery.

Figure 2:
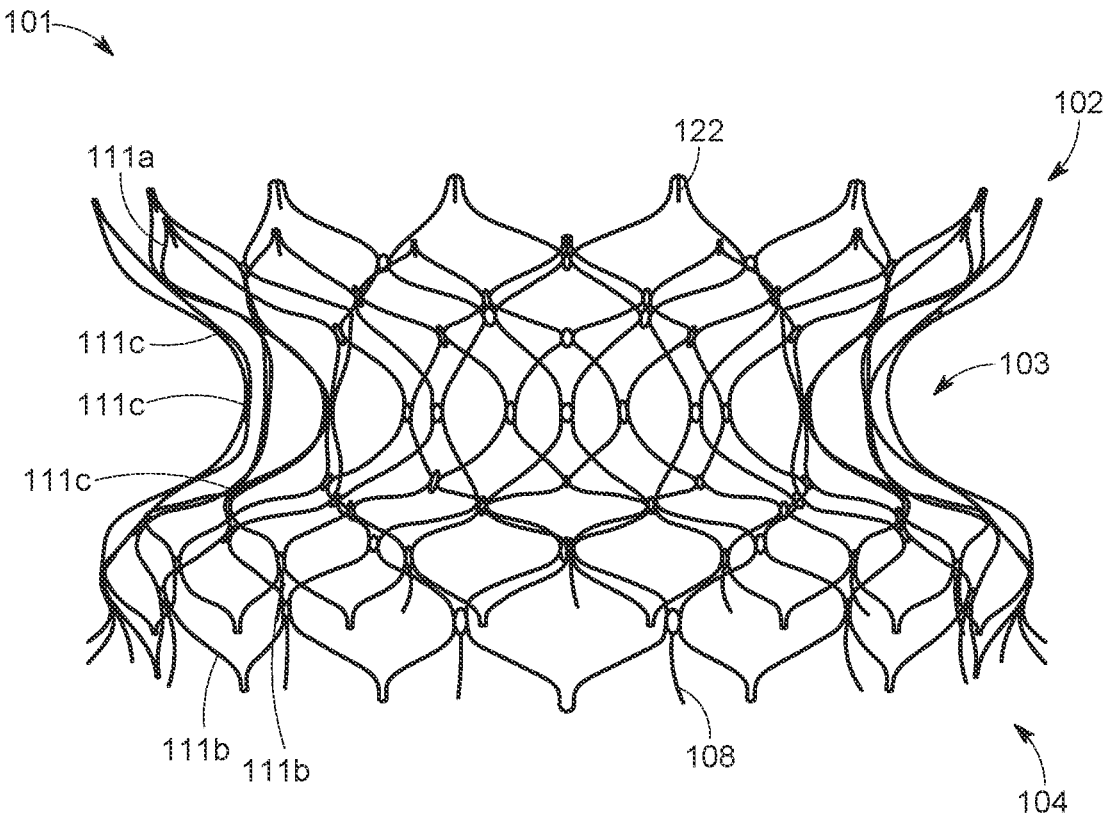
FIG. 2 is a side view of an example of an outer or anchoring frame that may be used as part of a prosthetic tricuspid heart valve.

FIG. 2 is a side view of an exemplary anchoring or outer frame that may be used as part of the prosthetic tricuspid heart valve system described herein. Anchor frame 101 is illustrated in an expanded condition in FIG. 2. The anchor frame 101 may be formed, in one example, via laser cutting a tube of shape memory material, such as a nickel-titanium alloy, including nitinol, to form a stent or stent-like structure. After being formed, the anchor frame 101 may be shape-set to the expanded condition, and the anchor frame 101 also has a collapsed condition in which the stent is collapsed to a smaller size from its expanded condition for transcatheter delivery to the patient. Anchor frame 101 may include an atrial portion or anchor 102, a ventricular portion or anchor 104, and a central portion 103 coupling the atrial portion to the ventricular portion. The central portion 103, which may also be referred to herein as a waist or central waist, may be between atrial portion 102 and ventricular portion 104. Atrial portion 102 may be configured and adapted to be disposed on an atrial side of the tricuspid valve annulus, and may flare radially outwardly from the central portion 103. Ventricular portion 104 may be configured and adapted to be disposed on a ventricle side of the native tricuspid valve annulus, and may also flare radially outwardly from the central portion 103. This shape may help to self-center the anchor frame 101 upon deployment, with the native tricuspid valve annulus being "sandwiched" or otherwise compressed between the atrial portion 102 and ventricular portion 104. The term "sandwiched" does not require mechanical action or other active compression, and may include the atrial portion 102 and the ventricular portion 104 simply being positioned on opposite sides of the annulus and in contact with the annulus.

The atrial portion 102 may be formed as a portion of a stent or other support structure that includes or is formed by a plurality of generally diamond shaped cells, although other suitable cell shapes, such as triangular, quadrilateral, or polygonal may be appropriate. In some examples, the atrial portion 102 may be formed as a braided mesh, as a portion of a unitary stent, or a combination thereof. According to one example, the stent that includes the atrial portion 102 may be laser cut from a tube of nitinol and heat set to a desired shape so that the stent, including atrial portion 102, is collapsible for delivery, and re-expandable to the set-shape during deployment. The atrial portion 102 may be heat set into a suitable shape to conform to the native anatomy of the tricuspid valve annulus to help provide a seal and/or anchoring between the atrial portion 102 and the native tricuspid valve annulus.

The atrial portion 102 may include features for connecting the atrial portion to a delivery system. For example, the atrial portion 102 may include pins or tabs 122 around which sutures (or suture loops) of the delivery system may wrap, so that while the suture loops are wrapped around the pins or tabs 122, the anchor frame 101 maintains a connection to the delivery device. However, in some embodiments, these pins or tabs 122 may be omitted.

The ventricular portion 104 may also be formed as a portion of a stent or other support structure that includes or is formed of a plurality of diamond shaped cells, although other suitable cell shapes, such as triangular, quadrilateral, or polygonal may be appropriate. In some examples, the ventricular portion 104 may be formed as a braided mesh, as a portion of a unitary stent, or a combination thereof. According to one example, the stent that includes the ventricular portion 104 may be laser cut from a tube of nitinol and heat set to a desired shape so that the ventricular portion 104 is collapsible for delivery, and re-expandable to the set-shape during deployment. It should be understood that the atrial portion 102 and ventricular portion 104 may be formed as portions of a single support structure, such as a single stent or braided mesh. However, in other embodiments, the atrial portion 102 and ventricular portion 104 may be formed separately and coupled to one another. It should also be understood that the atrial portion 102 (which may be referred to as a disk) and the ventricular portion 104 (which may also be referred to as a disk) may each be substantially symmetric, or otherwise may each be asymmetric. As an example, there is only minimal annulus structure close to the atrial septum, and thus it may be preferably to have smaller stent cells and/or a smaller disk diameter in this region of the atrial disk, resulting in an asymmetric atrial disk. This may also mean that that the anchoring stent 101 should be loaded in a certain orientation within the delivery device, or that the anchoring stent 101 can be rotated or will self-align so that the anchoring stent 101 is deployed in the desired rotational orientation relative to the patient's anatomy. And even if the atrial or ventricular disks are cut in a symmetric pattern, it might be desirable to heat set one or both structures so that the disks are asymmetric in their pre-set shape, for example curving more up or down compared to the rest of the structure. Also, it may be desirable that the cells in the atrial disk that are to be positioned closest to the atrial septum are softer to avoid any damage to the septal wall.

The anchor frame 101 may be configured to expand circumferentially (and radially) and foreshorten axially as the anchor frame 101 expands from the collapsed delivery configuration to the expanded deployed configuration. In the particular illustrated example, the anchor frame 101 includes or defines plurality of atrial cells 11a in one circumferential row and a plurality of ventricular cells 111b in two circumferential rows. Each of the plurality of cells 111a, 111b may be configured to expand circumferentially and foreshorten axially upon expansion of the anchor frame 101. As shown, the cells 111a-b may each be diamond-shaped. In addition, a third plurality of cells 111c may be provided in additional circumferential rows, in this embodiment three additional center rows, forming the central portion 103, also referred to as the waist.

Still referring to FIG. 2, a pin or tab 122 may extend from an apex of each atrial cell 111a in a direction toward the outflow end of the anchor frame 101. Although one pin or tab 122 is illustrated in each atrial cell 111a, in other embodiments fewer than all of the atrial cells may include a pin or tab, and in some embodiments the pins or tabs 122 may be completely omitted. In addition, each ventricular cell 111b may include a tine or barb 108 extending therefrom. In the illustrated embodiment, each tine extends from a point where two adjacent ventricular cells 111b in the terminal outflow row of cells meet one another, or otherwise from the outflow apex of a ventricular cell 111b in the second row of ventricular cells (e.g. the row of ventricular cells directly adjacent, in the inflow direction, to the terminal outflow row of ventricular cells 111b). However, fewer than all of the ventricular cells 111b cells may include such tines or barbs. In the expanded condition of the anchor frame 101, as shown in FIG. 2, the barbs 108 may hook outwardly, the barbs being configured to pierce native tissue of the tricuspid valve annulus, such as the native leaflets, to help keep the prosthetic heart valve from migrating under pressure during beating of the heart. Typically, the term "tine" may refer to a structure configured to pierce into tissue, while the term "barb" may refer to a tine that also includes a barb-like structure to prevent the barb from pulling out of the tissue once pierced. However, as used herein, the term "barb" includes tines, with or without actual "barb"-like structures that prevent pulling out of tissue, unless specifically noted otherwise. Further, it should be understood that the barbs and/or tines do not need to actually pierce tissue to help resist migration—rather the barbs and/or tines may make direct contact with the tissue without actually piercing the tissue. Either piercing, or direct contact without piercing, may serve to increase valve migration resistance. However, it should be understood that the tines 108 may be fully omitted from anchor frame 101 without a loss in the ability of the anchor frame 101 to suitably anchor the valve component (described in greater detail below) without migration toward the right atrium. While tines or barbs have been used in prosthetic mitral valves to help resist atrial migration, the relatively low pressures experienced in the right heart may allow for the omission of such tines or barbs if desired. It should be understood that FIG. 2 only illustrates the metallic scaffold that forms the anchor frame 201 (which may be referred to as a stent), but other features including fabric skirts may be included, such as those shown and described in connection with FIGS. 3-4 below. Although the tines 108 are shown as being generally uniformly distributed around the ventricular disk, the tines 108 do not need to be uniformly distributed. For example, in order to avoid interference with the conductive system of the patient's heart, it may be desirable if, in the area of the AV node or the bundle of His, tines 108 are omitted, or the tines 108 in that location are formed with a different shape or structure to help avoid electrical interference with the conduction system of the heart. Although tines 108 are shown as extending from the location where two adjacent diamond-shaped cells meet each other, in some embodiments, if tines are included, they may extend from the outflow apices of the diamond-shaped cells in the outflow row of cells.

FIG. 3 is a cross-section of an anchor frame 201 according to another aspect of the disclosure. As shown in FIG. 3, anchor frame 201 includes a flared atrial disk or atrial portion 202, a flared ventricular disk or ventricular portion 204, and a narrow waisted central portion 203. The overall shape and structure of anchor frame 201 may be generally similar to that of anchor frame 101, and is thus not described again herein, other than to note that anchor frame 201 may be formed of a shape memory material such as an nitinol, and formed with a braided mesh or laser cut from a tube of nitinol, for example with generally diamond-shaped cells that are shape-set to have the generally hourglass shape shown in FIG. 3 in the absence of applied forces. In other words, anchor frame 101 and anchor frame 201 may be part of the same structure, but the illustration and description of anchor frame 101 focus on the stent or scaffolding component, while the illustration and description of anchor frame 201 focus on the other components that may be provided with the stent or scaffolding. As will become clear, anchor frames 101, 201 are not designed for direct coupling to an inner valve component, but rather to act as a first stage implant, to which a valve component is later secured. In this respect, anchor frames 101, 201 may be thought of as a "dock" for a prosthetic valve component.

Anchor frame 201 may include one or more fabric components that may provide one or more functions, for example including sealing. In the illustrated embodiment, the anchor frame 201 may include a sealing skirt 220 on a luminal and/or abluminal surface thereof. This sealing skirt 220 may be generally similar to other sealing skirts provided on stents or frames of transcatheter prosthetic heart valves. This luminal and/or abluminal sealing skirt 220 may be formed of any suitable material, including biomaterials such as bovine pericardium, biocompatible polymers such as ultra-high molecular weight polyethylene, woven polyethylene terephthalate ("PET") or expanded polytetrafluoroethylene ("ePTFE"), or combinations thereof. The sealing skirt 220, particularly if positioned on the abluminal surface of the anchor frame 201, may include a "bump" (or gasket or ring) portion to enhance sealing, similar to that described in U.S. patent application Ser. No. 17/548,984, the disclosure of which is hereby incorporated by reference herein. In addition to sealing skirt 220, the anchor frame 201 may include an atrial sheet 230 and a ventricular sheet 240. In some embodiments, any combination of sealing skirt 220, atrial sheet 230, and ventricular sheet 240 may be formed as an integral member, although in other embodiments, the atrial sheet 230 and ventricular sheet 240 are formed of different materials that provide different functionality, and are not formed as integral members.

Referring still to FIG. 3, atrial sheet 230 may have a radially outward portion (e.g. an outer circumferential area) coupled to the atrial portion 202, for example by suturing, and extend radially inwardly toward a central longitudinal axis where a central aperture is formed in the atrial sheet 230. But for the central aperture, the atrial sheet 230 may be thought of as a membrane not dissimilar to the head or skin of a drum. The ventricular sheet 240 may similarly have a radially outward portion (e.g. an outer circumferential area) coupled to the ventricular portion 204, for example by suturing, and extend radially inwardly toward a central longitudinal axis where a central aperture is formed in the ventricular sheet 240. In other words, the atrial sheet 230 and ventricular sheet 240 may have substantially similar constructions, although they may be formed of different materials to provide different functionalities, preferably with the central apertures being substantially coaxial with each other when the anchoring frame 201 is in the expanded or deployed condition.

A valve-receiving member 250, which may be generally cylindrical, may have a first inflow end coupled to the atrial sheet 230 so that the first inflow end is substantially coextensive with the central aperture of the atrial sheet 230, and a second outflow end coupled to the ventricular sheet 240 so that the second outflow end is substantially coextensive with the central aperture of the ventricular sheet 240. The valve-receiving member 250 is preferably formed of a fabric, such as PTFE, UHMWPE, Kevlar braid, Dacron, or biomaterials such as tissue. In some embodiments, the valve-receiving member 250 may be formed of a thin wires of nitinol, stainless steel, or other biocompatible metals or metal alloys formed into a braided, knitted, or woven structure. The inflow and outflow ends of the valve-receiving member 250 may be coupled to the atrial sheet 230 and ventricular sheet 240, respectively, by any suitable means including sutures. For example, in some embodiments, an inflow end of the valve-receiving member 250 may be suspended via sutures that extend radially outwardly and connect to the atrial portion 202, and the outflow end of the valve-receiving member 250 may be suspended via sutures that extend radially outwardly and connect to the ventricular portion 204. In this embodiment, the suspension sutures may have a "spoke" configuration, or in other embodiments one or more layers of continuous suture loops may be used. Other examples of suspending an inner valve portion (or valve-receiving portion) within an anchor frame are described in more detail in U.S. Provisional Patent Application No. 63/376,496, titled "Prosthetic Tricuspid Heart Valve," and filed Sep. 21, 2022, the disclosure of which is hereby incorporated by reference herein.

An example of this "spoke" configuration described above is shown in FIGS. 14A-B. FIG. 14A schematically shows a plurality of individual radially extending sutures S each having a first end coupled to the valve-receiving member 250 and a second end connected to the anchoring frame. FIG. 14B illustrates a view from the ventricular end, showing the sutures S radially extending between the valve-receiving member 250 and the ventricular portion 204 of the anchor frame 201. Although FIG. 14A shows single sutures S, groups of sutures S may be provided as shown in FIG. 14B. For example, FIG. 14B illustrates a group of radially extending sutures extending from each cell in the ventricular portion 204 to the valve-receiving member 250 to suspend the valve-receiving member 250 within the frame. These sutures S may be tied off on the stent frame and may provide a large amount of axial support to the valve-receiving member 250.

An example of the continuous suture loop configuration described above is shown in FIGS. 15A-C. FIG. 15A is a schematic view illustrating a single continuous suture S that extends from the valve-receiving member 250 to the frame, which then loops back to the valve-receiving member 250, with the looping continuing around the circumference of the anchor frame 201. Preferably, a number of continuous sutures S are provided at different axial heights of the anchor frame 201. For example, as shown in FIGS. 15B-C, five continuous suture loops S1-S5 may be used, which each continuous suture loop being positioned at a different axial height. However, it should be understood that more or fewer than five continuous suture loops S1-S5 may be used. In the illustrated embodiment of FIGS. 15B-C, two suture loops S1-S2 are provided on or adjacent to the atrial portion 202, one suture loop S3 is provided at the central waist 203, and two suture loops S4-5 are provided on or adjacent to the ventricular portion 204. As with the radially extending sutures S, the circumferentially continuous sutures may allow the valve-receiving member 250 to be securely suspended within the frame, and minimize axial motion of the valve-receiving member relative to the frame as the heart cycles between systole and diastole.

Preferably, a support wire 260 is provided around the circumference of the valve-receiving member 250 at its outflow end, with another support wire (not labeled in FIG. 3) provided around the circumference of the valve-receiving member 250 at its inflow end. Although the term "support wire" is used, it should be understood that the term "wire" does not require a specific material, and a support wire may be a loop, and the loop may be formed of any suitable material, including metal wires, flexible cables, sutures, monofilaments, multi-filaments, etc. For example, the support wires 260 may each be a strong suture (e.g. 2-0 suture) or a flexible metal cable, which may be woven circumferentially into the valve-receiving member 250. As will be described in greater detail below, the support wires 260 may assist in anchoring a valve component that is expanded (e.g. balloon expanded or self-expanded) into the valve-receiving member 250 after the anchor frame 201 is deployed within the native tricuspid valve. At least in part because the valve-receiving member 250 is suspended within the anchor frame 201 via atrial sheet 230 and ventricular sheet 240, the valve component eventually received within the valve-receiving member 250 will retain its shape, even if the native tricuspid valve deforms the shape of the anchor frame 201, for example from forces as the heart beats. In other words, the shape of the valve component within the valve-receiving member 250 is substantially independent of the shape of the anchor frame 201. This may be desirable because the valve component will typically have a circular shape or profile, and it is desirable to maintain that circular shape or profile to help ensure that the prosthetic leaflets of the valve component are able to coapt to prevent regurgitation across the prosthetic leaflets. If forces on the anchor frame 201 were transmitted to the valve component in the valve-receiving member 250, and the valve component were to be deformed, the prosthetic leaflets of the valve component may not be able to coapt correctly.

Although not required, it may be desirable to include radiopaque markers 270 on both the inflow end of the valve-receiving member 250 and the outflow end of the valve-receiving member 250. These radiopaque markers 270 may be formed of any biocompatible substance that are easily visualized during imaging, and have any desired configuration. For example, the radiopaque markers 270 may be small pieces of biocompatible metal coupled to the valve-receiving member or may be radiopaque threads that are sutured into the valve-receiving 250, although other configurations may be appropriate. These radiopaque markers 270 may readily show, during imaging, where the ends of the valve-receiving member 250 are located so that the valve component may be reliably and desirably positioned within the valve-receiving member 250 prior to expansion of the valve component.

It may be desirable that, when the anchor frame 201 is deployed in the native tricuspid valve annulus, the valve-receiving member 250 does not "bunch up" or buckle. This may be a concern, particularly if the valve-receiving member 250 is formed of a fabric. Rather, it is preferable that the valve-receiving member 250 be smooth and fully axially extended and suspended between the atrial sheet 230 and ventricular sheet 240 upon deployment of the anchor frame 201. In order to facilitate this, stretching or stiffening elements 280 may be provided in or on the valve-receiving member 250, although such features are not required in all embodiments. In the illustrated embodiment, a metal structure, such as nitinol, is either woven into, or sutured onto, the fabric forming the valve-receiving member 250, with the stretching element(s) 280 generally extending in the axial direction from the inflow end of the valve-receiving member 250 to the outflow end of the valve-receiving member 250. By having the stretching element(s) extend axially, they will help ensure that the valve-receiving member 250 stretches axially, or at least does not bunch up, upon deployment of the anchor frame 201. Still further, this axial positioning will help ensure that there will be no (or no significant) increase in force required to crimp the anchor frame 201 down to the collapsed condition for delivery. It should be understood that other materials may be suitable for the stretching or stiffening elements 280, such as polymeric materials, small carbon tubes, metals, plastic, ceramics, etc. If these elements are oriented parallel to the longitudinal axis, there is no need for the elements to lengthen or foreshorten when the anchor frame 201 is crimped or otherwise collapsed. Other features, such as support arms 500 and support arms 600, described in greater detail below in connection with FIGS. 8A-9C, may provide some common functionality as the stretching or stiffening elements 280.

Compared to a typical prosthetic heart valve frame that requires (1) structures to directly support prosthetic leaflets, such as commissure attachment features and/or (2) structures to allow for direct coupling to an inner valve, the anchor frame 201 (which requires neither) can be formed of substantially less metal, and thus can have a significantly smaller crimp profile when in the collapsed condition. For example, the collapsed size of the anchor frame 201 may be about 30 French (10 mm) or less.

Figure 4:
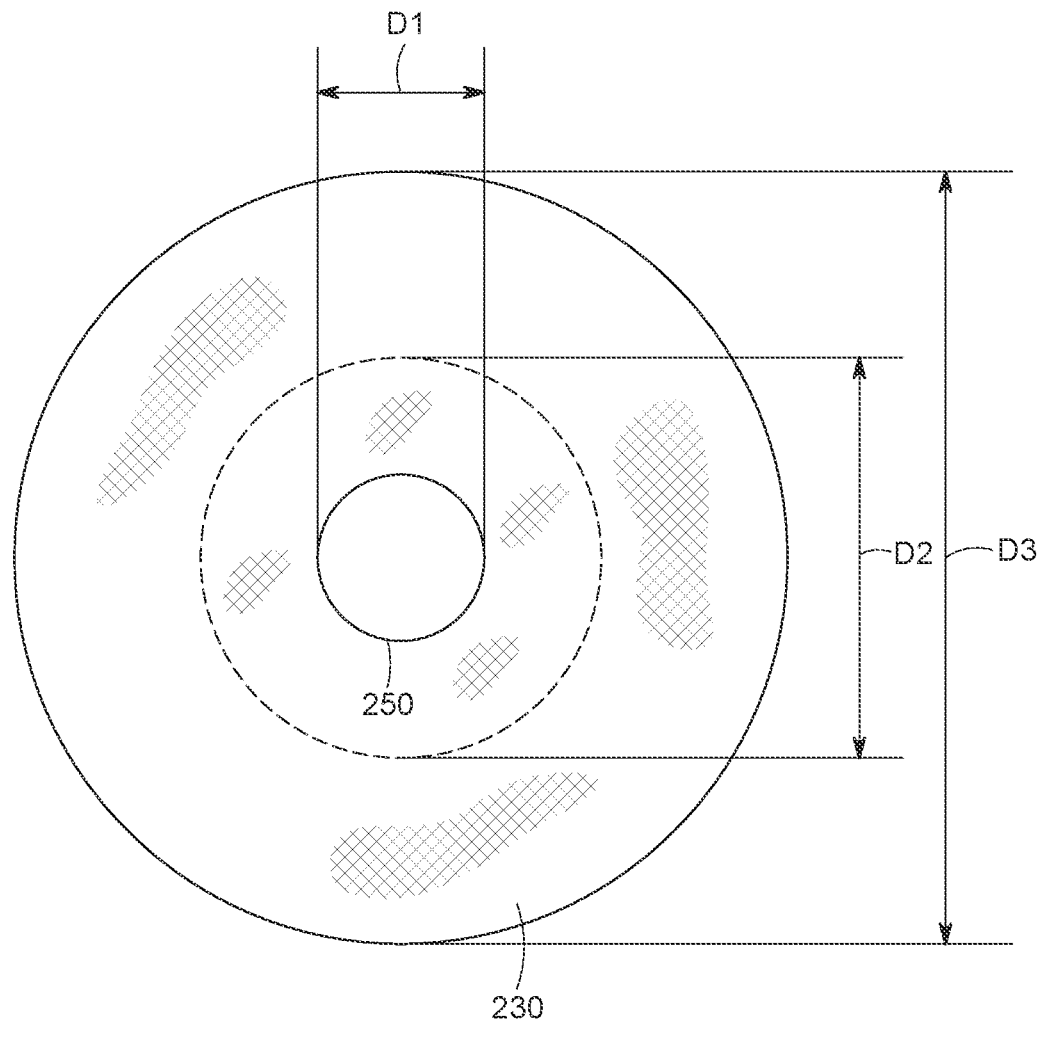
FIG. 4 is a top view of the anchor frame of FIG. 3.

FIG. 4 is a top view (of the atrial side) of the anchor frame 201 when in the expanded condition. As shown, the valve-receiving portion 250 results in an open passageway axially through the anchor frame 201. As is described in greater detail below, this results in there being no valve functionality for the entire time that the valve-receiving portion 250 remains open (e.g. without a valve component deployed therein). The diameter D1 of the valve-receiving portion 250 is preferably between about 20 mm and about 40 mm, including between about 25 mm and 35 mm, and preferably between about 27 mm and about 33 mm, including about 28 mm, about 29 mm, about 30 mm, about 31 mm, and about 32 mm. The diameter D2 of the central waist 203 may be provided based on the size of the patient's tricuspid valve annulus. In some examples, the diameter D2 of the central waist 203 may be between about 30 mm and about 70 mm, including between about 36 mm and about 60 mm. The diameter D3 of the atrial portion 202 and ventricular portion 204 may also depend on the size of the diseased tricuspid valve, and different sizes may be provided. For example, the diameter D3 of the atrial portion 202 and ventricular portion 204 may be about 50 mm or larger, including up to about 65 mm or even up to about 75 mm for extreme cases. It should be understood that, although a plurality of anchoring frames 201 may be provided with different diameters D2 and D3 (see, e.g., FIGS. 3-4) so that a particularly sizing combination may be chosen for a particular patient's anatomy, it is generally preferable that only a single size diameter D1 of the valve-receiving portion 250 is provided, as the valve-receiving portion 250 may be configured to receive a single size valve component that is not dependent upon the size of the patient's tricuspid valve annulus. It should also be understood that, even though the term "diameter" is used, in some embodiments the atrial and ventricular disks may not be circular and may be asymmetric as described above.

In an exemplary use of anchoring frame 201, it may first be transitioned to a collapsed condition and placed within a sheath of a delivery device, the sheath maintaining the anchoring frame in the collapsed condition. The sheath of the delivery device may have an outer diameter of around 30 French (10 mm) or smaller, including about 28 French (9.333 mm), and be introduced into the femoral vein without the need for a surgical cut down of the femoral vein. However, in some embodiments the sheath may have a diameter of between 18 French (6 mm) and about 28 French (9.333 mm), below 18 French (6 mm), or above 30 French (10 mm). The delivery device may be advanced through the patients vasculature, through the inferior vena cave, into the right atrium, and may be oriented (for example via a steering mechanism) so that the distal end of the sheath is within or adjacent to the native tricuspid valve annulus. The distal end of the sheath may be withdrawn relative to the anchoring frame 201, removing the constraint on the anchoring frame 201 and allowing the anchoring frame 201 to begin to self-expand into the native tricuspid valve annulus, with the ventricular portion 204 abutting the ventricular side of the valve annulus, the atrial portion 202 abutting the atrial side of the valve annulus, and the valve annulus received within the waisted central portion 203. When deployed, the anchor frame 201 may provide reliable anchoring via (i) the pinching of the native tricuspid valve annulus by the atrial portion 202 and the ventricular portion 204; (ii) the oversizing of the central waist portion 203 relative to the native tricuspid valve annulus; and/or (iii) anchoring tines or barbs, if included. While the anchor frame 201 is deployed, and before the valve component is deployed into the valve-receiving member 250 (which may be referred to as the first phase of implantation), the valve-receiving member 250 provides an open conduit between the right ventricle and the right atrium.

Before describing the second phase or stage of implantation, in which a valve component is deployed into the anchor frame 201, certain concepts and features related to the existence of the open conduit (after the first phase of implantation) are described. Although two-stage prosthetic valve implantations that utilize docking stations have been described in the past in the context of aortic valves and mitral valves, those two-stage prosthetic valve implantations generally include (1) temporary leaflets that provide valve functionality between the two stages; (2) a very short time between the completion of the first stage and the second stage, on the order of seconds (e.g. one minute or less); and/or (3) preservation of the function of the native valve leaflets. The reasoning behind the above points is that, while open communication is created between the left atrium and the left ventricle (or between the left ventricle and the aorta), the lack of valve functionality may lead to patient death if the duration is longer than a minute or two, although even a minute or two may be an unacceptably long time. For example, the lack of valve functionality between the left atrium and the right atrium for even 10 to 15 seconds may be an unacceptable risk. Put simply, the heart is not pumping blood if the aortic valve or mitral valve cannot close. And although secondary mechanisms (e.g. an inter-aortic balloon pump) may be used to pump blood while the native leaflets are not functioning, such additional components may add extra complexity, cost, and/or risk to the procedure. However, the tricuspid valve may not suffer from this same issue, at least not to the same degree. Counterintuitively, although the purpose of the prosthetic tricuspid valve system implantation is to reduce or eliminate backflow between the right atrium and the right ventricle, it may not be a significant problem to leave the anchor frame 201 within the native tricuspid valve without completing the second stage of implantation for an extended period of time. In fact, there may even be benefits that arise from delaying the second stage of prosthetic tricuspid valve implantation for a duration of multiple minutes, hours, or even days after the first phase is completed and there is effectively no valve functionality between the right atrium and the right ventricle. This is due, at least in part, to the different hemodynamics between the relatively low pressure right heart and relatively high pressure left heart. For example, even with the native tricuspid valve leaflets forced open by the anchor frame 201, a relatively healthy left heart can pump blood through the vasculature to reach the right side of the heart, and then into the lungs, with the help of the pulmonary valve, despite the torrential tricuspid regurgitation from the lack of tricuspid valve functionality. While the efficiency of the heart may be very poor in this condition, the patient may be able to survive days or even weeks, compared to potentially being able to survive for a minute or two if the mitral or aortic valves were providing no valve functionality.

As noted above, there may even by benefits of intentionally delaying the amount of time between the completion of the first phase of implantation and the second phase of implantation. One such benefit may be an increase in stability of the anchor frame 201, including for example via tissue ingrowth. In one example, the atrial sheet 230 may be formed of a permeable or porous fabric, such as a polyester, while the ventricular sheet 240 may be formed from a substantially nonporous or liquid-impermeable material, such as a tightly woven and/or coated PTFE. The pores in the atrial sheet 230 may be sized so that blood can pass through the atrial sheet 230, but if blood clots within the space between the atrial sheet 230 and ventricular sheet 240, the pores are too small to allow thrombi to pass through the atrial sheet 230. While liquid blood may cross the atrial sheet 230, it cannot cross the ventricular sheet 240 with the above configuration due to the nonporous or liquid-impermeable nature of the ventricular sheet 240. After the anchor frame 201 is implanted, blood may tend to coagulate between the atrial sheet 230 and ventricular sheet 240, and blood may also effectively coagulate on the atrial sheet 230 itself. The coagulated blood may provide a semi-rigid support for the prosthetic heart valve later implanted into the valve-receiving member 250. If this process is allowed to continue for a length of time, the anchor frame 201 may become more stable over time, with at least some additional stability coming from tissue ingrowth. In other words, if the second stage of the implantation is intentionally delayed, the anchor frame 201 may be more stable when it is time to actually complete the second stage and implant or "dock" the valve component into the anchor frame 201. The above-noted stability may include a reduction in axial motion of the valve-receiving member 250 relative to the anchoring support after the prosthetic heart valve is implanted into the valve-receiving member 250 and the heart cycles between systole and diastole. FIGS. 13A-B illustrate such an embodiment with a permeable atrial sheet 230 and an impermeable ventricular sheet 240. FIG. 13A illustrates the configuration prior to blood coagulating within the volume between the two sheets, and FIG. 13B illustrates the configuration after blood has coagulated within the volume between the two sheets. It should be understood that, although in some embodiments the atrial sheet 230 may be formed of a porous fabric and the ventricular sheet 240 may be formed of a fluid-impermeable material, in some embodiments the atrial sheet 230 may be formed of a fluid-impermeable material and the ventricular sheet 240 may be formed of a porous fabric.

Another potential benefit of intentionally delaying the amount of time between the completion of the first phase of implantation and the second phase of implantation is allowing the heart to acclimate to new flow dynamics over time. For example, in patients with severe or torrential tricuspid regurgitation, there may actually be a danger of transitioning between extreme tricuspid regurgitation and minimal or no regurgitation in what is essentially an instantaneous change upon implantation of a prosthetic tricuspid valve. This potential danger lies, at least in part, in the fact that the flow dynamics change nearly instantaneously, while the heart muscle cannot acclimate instantaneously. As an example, a patient with severe or torrential tricuspid regurgitation may have a relatively thin right ventricle due to dilation from heart failure. However, after tricuspid regurgitation is resolved, pressures within the right ventricle may increase, putting the patient at risk of right ventricular rupture or further dilation. This may place undue strain on the right ventricle. In some instances, particularly in cases of torrential tricuspid regurgitation, even when the native tricuspid valve should be closed, the opening at the native tricuspid valve is large—even greater than the about 28 mm to about 32 mm diameter D1 of the valve-receiving member 250. In other words, even prior to completing the second stage of implantation, simply deploying the anchor frame 201 may decrease the amount of regurgitation across the tricuspid valve. With this decrease in regurgitation, resistance is increased with the right ventricle contracts, which may allow the right ventricle to strengthen and/or thicken over a period of days prior to the completion of the second stage of implantation. During this time between the two stages, then, the right ventricle may begin to acclimate to the new hemodynamics, so that after completion of the second stage of implantation, the right ventricle has already gotten stronger and is more "ready" for the change in hemodynamics that occur after completion of the second phase of implantation. However, even if it is unlikely that the size of the open conduit of the valve-receiving member 250 would create a reduction in the patient's tricuspid regurgitation, other mechanisms, such as temporary leaflets described below, may be used to create a step-wise reduction in tricuspid regurgitation by delaying the time between the first and second stages of implantation.

Now continuing the above exemplary use description, the first phase of implantation has been completed and the anchor frame 201 is deployed within the native tricuspid valve annulus, with the valve-receiving member 250 creating an open conduit between the right atrium and the right ventricle. At some point after this first phase, the second phase of implantation may begin. As noted above, the timing choice between completion of the first phase and beginning of the second phase may vary. In some circumstances, it may be desirable to finish the first phase of implantation, withdraw all devices from the patient, and allow time on the order of hours, days, or even a week or more to pass before beginning the second phase of implantation in what is effectively a fully separate procedure. In other circumstances, there may be little or no delay between completing the first stage of implantation and beginning the second stage of implantation. It should also be understood that, even if the anchor frame 201 is implanted and allows an open conduit between the right atrium and ventricle for an amount of time (even if hours, days, or weeks), there may be no assistive device (e.g. a mechanical pump) used during the amount of time the open conduit remains in place.

Figure 5:
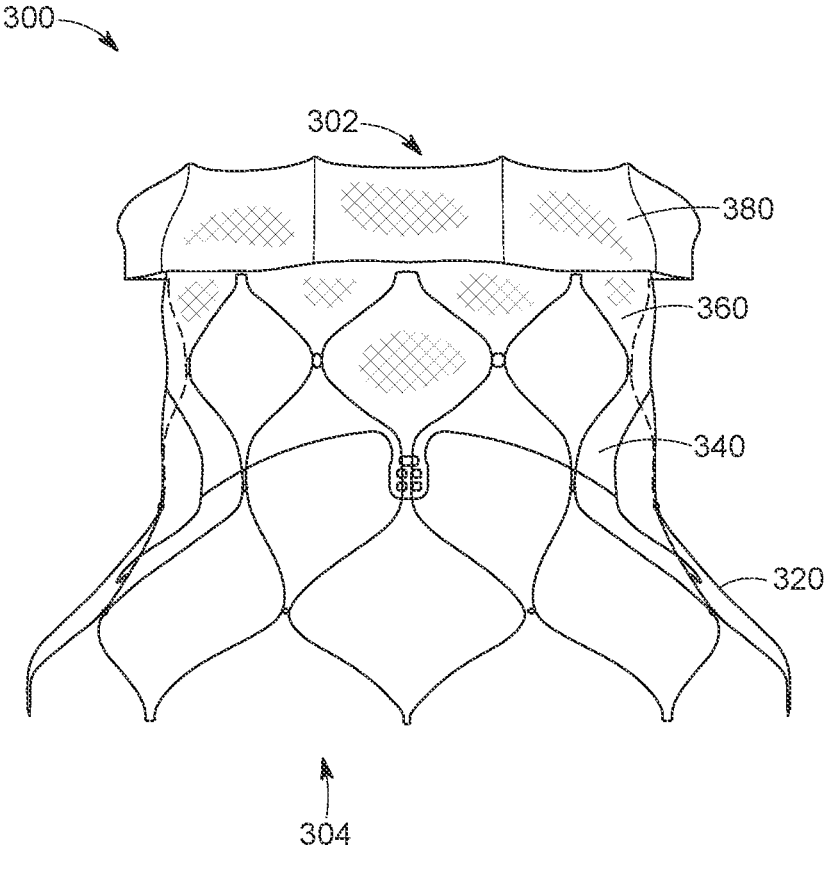
FIG. 5 is a side view of a valve component that may be used with the anchor frame(s) of FIGS. 2-4.

In the second stage of implantation, a valve component 300 is deployed into the anchor frame 201. FIG. 5 illustrates on exemplary valve component 300, but it should be understood that other configurations of valve components may be utilized in a similar or identical fashion. Referring to FIG. 5, a valve component 300 is illustrated that is similar to the Navitor™ prosthetic heart valve offered by Abbot Labs. Generally speaking, valve component 300 extends from an inflow end 302 to an outflow end 304, and includes a stent 320, a plurality of prosthetic leaflets 340 (in this embodiment, three prosthetic leaflets 340, preferably formed of pericardial tissue or synthetic biocompatible materials), an inner skirt or cuff 360 on a luminal surface of the stent 320, and an outer skirt or cuff 380 on an abluminal surface of the stent 320. In this particular example, stent 320 has a generally cylindrical annulus portion nearer the inflow end 302 and an outwardly flared outflow portion nearer the outflow end 304. Further, in this particular example, stent 320 is formed of a shape memory material, such as a nickel titanium alloy, such as nitinol, so that the valve component 300 is self-expanding. However, in other embodiments, the stent 320 may have other shapes, including generally cylindrical. Still further, in other embodiments, the stent 320 may be formed of a plastically expandable material, such as stainless steel, cobalt chromium, or other metals or metal alloys that are plastically expandable, so that the valve component 300 is balloon expandable.

The prosthetic leaflets 340 may have, in the aggregate, a generally cylindrical profile, with three leaflets total, each leaflet coupled to an adjacent leaflet at a commissure feature of the stent 320. However, more or fewer prosthetic leaflets 340 may be provided as desired. The inner cuff 360 may be formed of biocompatible tissue or synthetic material, such as PTFE, PET, or ultra-high molecular weight polyethylene (UHMWPE). The outer cuff 308 may similarly be formed of biocompatible tissue or synthetic material, such as PTFE, PET, or UHMWPE. In the illustrated configuration, the outer cuff 308 has an inflow edge that is fixed (e.g. via suturing) to the inner cuff 360 and/or the stent 320, with an outflow edge that is coupled to the inner cuff 360 and/or stent 320 at spaced apart circumferential locations, to create one or more openings between the outer cuff 380 and the inner cuff 360 into which blood may flow. If blood flows into these openings, e.g. during retrograde blood flow, the outer cuff 380 may billow outwardly to help ensure there is no regurgitation around the outside of the valve component 300. Additional details that may be relevant for use with valve component 300 are described in greater detail in U.S. Pat. No. 10,548,722, the disclosure of which is hereby incorporated by reference herein.

The valve component 300 may be collapsed to a small diameter and positioned within the sheath of a delivery device and introduced into the right heart via any suitable means and delivery route. For example, the valve component 300 may be delivered via the femoral vein, similar to anchor frame 201, via a transapical access route through the chest and through the right ventricle, via a transjugular delivery route and through the superior vena cava, or any other desirable delivery route that leads to the tricuspid valve. In some circumstances, particularly if the second stage implantation is being performed immediately after the first phase, the same catheter may even be used for each stager of implantation, although this is not required.

Regardless of the delivery route, the distal end of the delivery catheter housing the collapsed valve component 300 is positioned adjacent to, or within, the valve-receiving member 250 of the anchor frame 201.

If valve component 300 is self-expandable, the catheter sheath may be withdrawn or advanced to uncover the valve component 300, removing the constriction maintaining the valve component 300 in the collapsed condition, thus allowing the valve component 300 to self-expand into the valve-receiving member 250. Upon self-expansion, one or both of the support wires 260 helping anchor the valve component 300 within the anchor frame 201. If the stent 320 of valve component 300 includes the outwardly flared outflow section, the outward flare may protrude beyond the outflow end of the valve-receiving member 250 and provide additional anchoring force to resist migration toward the right atrium. However, in other embodiments, the outwardly flared outflow section may be omitted, with the stent being generally cylindrical.

If valve component 300 is balloon-expandable, the valve component 300 may be crimped over an uninflated balloon when the valve component 300 is within the delivery catheter in the collapsed condition. Examples of balloon-expandable valves that may be used as a second stage implant are described in greater detail in U.S. Provisional patent application Ser. No. 17/381,358, the disclosure of which is hereby incorporated by reference herein. However, if the valve component 300 is balloon-expandable it may or may not be covered by a catheter sheath during the second stage implant. Rather than withdrawing a sheath to allow the valve component 300 to self-expand, the balloon is inflated (e.g. by pushing saline through the delivery device into the balloon) to force the valve component 300 to expand into the valve-receiving member 250 of the anchor frame 201. Regardless of whether the valve component 300 is self-expanding or balloon expandable, the radiopaque markers 270 on the inflow and/or outflow end of the valve-receiving member 250 (if included) may be referenced with imaging to confirm that the valve component 300 is in the desired position relative to the valve-receiving member 250 prior to expansion of the valve component 300. As the balloon inflates to force the valve component 300 to expand into the valve-receiving member 250 of the anchor frame 201, one or both support wires (or sutures) 260 will provide some resistance against the forces and help ensure that the forces do not simply cause the valve-receiving member 250 to expand and possibly rip, tear, or otherwise become damaged. The support wires 260, which each may have a generally circular profile, may also help ensure that upon expansion of the valve component 300, the valve component is generally cylindrical (e.g. with a circular profile). The support wires 260, at least in part, help ensure that the valve component 300 does not "ovalize" upon expansion. If the support wires 260 are formed of a material that has a slight stretch, such as the 2-0 suture noted above, the support wire 260 may stretch a small amount while maintaining the valve component 300 in the desired cylindrical or circular shape. However, it should be understood that the tubular fabric that forms valve-receiving member 250 may be strong enough, without the use of support wires 260, to suitably maintain the valve component 300 therein. And although one or both (or more) support wires 260 or loops are optional, the loop(s) may provide some benefit, particularly if the valve-receiving area can be stretched by the implanted valve. In this case the loop may prevent an overexpansion and might even allow that the inflow and outflow sections of the balloon expandable stent will flare outwardly and thereby improve anchoring.

Whether self-expanding or balloon-expandable, it is preferable that the valve component have a diameter (at least at the portion housing the prosthetic leaflets 340) of between about 25 mm and about 35 mm, including between about 28 mm to about 32 mm, including about 29 mm, about 30 mm, and about 31 mm.

After the valve component 300 is deployed within the anchor frame 201, the prosthetic leaflets 340 may take on the function of the previously failing native tricuspid valve leaflets. At this point, any remaining catheters or other accessories within the patient may be removed, and the procedure completed.

As should be understood from the above description, the use of anchor frame 201 may help reduce the need for any (or any significant) reliance on imaging to confirm anchoring upon deployment within the native tricuspid valve annulus. Additionally, because the native tricuspid valve leaflets are not used for obtaining the desired fixation of the anchor frame 201 within the native tricuspid valve annulus, the uncertainty regarding the number and particular configuration of a patient's native tricuspid valve leaflets does not negatively impact the procedure. Still further, because the anchor frame 201 and valve component 300 may be delivered at different times (whether seconds apart or weeks apart), the delivery device used to deliver each component may be small, for example under about 30 French (10 mm), which provides benefits including the ability to avoid a surgical cut down of the femoral vein.

As noted above, the atrial sheet 230 and ventricular sheet 240, when attached to the stent or scaffold of anchor frame 201, may have a configuration similar to the head or skin of a drum. While this may have a beneficial effect in helping to ensure that the valve component 300 within the valve-receiving member 250 remains in a circular profile or cylindrical shape even if the anchor frame 201 deforms, this "drumming" configuration may lead to some amount of instability of the valve component 300. For example, each time the heart beats (e.g. each time the right ventricle contracts), pressure against the closed prosthetic leaflets 340 of the valve component 300 may cause the valve component 300 and valve-receiving member 250 to temporarily move toward the right atrium, before the pressure is reduced and the valve component 300 moves back to a neutral position. In other words, because of a relatively "soft" connection between the stent or scaffolding of the anchor frame 201 and the valve component 300, the valve component 300 may rock up and down as the heart beats. In addition, there is a possibility that the valve component 300 may experience temporary tilting away from the central longitudinal axis of the native tricuspid valve annulus and/or temporary lateral motion as other forms of "rocking" as the heart beats.

Figure 7:
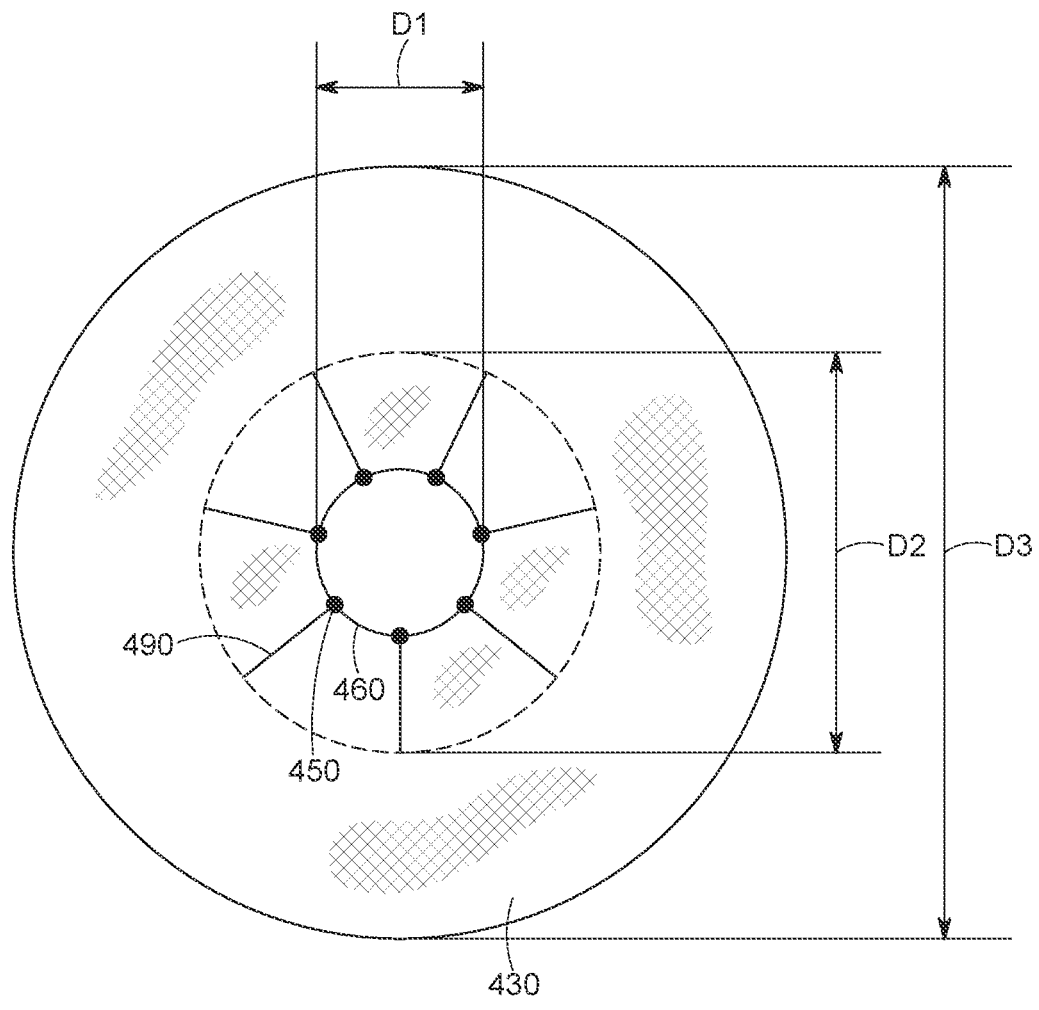
FIG. 7 is a top view of the anchor frame of FIG. 6.

One way to minimize or eliminate the likelihood of the valve component 300 rocking is to provide one or more support arms that directly connect the stent or scaffolding of the anchor frame 201 to the fabric valve-receiving member 250. FIG. 6 shows a cross-section, and FIG. 7 shows a top (atrial) view of an anchor frame 401 with one or more support arms 490 according to another aspect of the invention. It should be understood that, like anchor frame 201, anchor frame 401 may include a stent or scaffolding structure similar or identical to anchor frame 101. Also, anchor frame 401 has many similar or identical components to anchor frame 201, those similar or identical components provided with part numbers that are increased by 200. Thus, only the differences of anchor frame 401 compared to anchor frame 201 are described below, and the remaining components of anchor frame 401 may be similar or identical to those of anchor frame 201. It should further be understood that the exemplary use description of anchor frame 201 with valve component 300 may apply with substantially equal force to an exemplary use of anchor frame 401 with valve component 300.

Referring to FIG. 6, anchor frame 401 may include an atrial portion 402, central waist portion 403, and ventricular portion 404 similar or identical to the corresponding components of anchor frame 201. Anchor frame 401 may also include a sealing skirt 420, atrial sheet 430, and ventricular sheet 440 similar or identical to the corresponding components of anchor frame 201. Anchor frame 401 may also include support wires 460 similar or identical to the corresponding components of anchor frame 201. Stretching or stiffening elements similar to elements 280 of anchor frame 201 may or may not be included in similar configurations as described in connection with anchor frame 201. However, as should be clear, the support arms 490 described below may have a similar effect in maintaining the fabric valve-receiving member 450 in a stretched condition, obviating the need for additional stretching or stiffening elements similar to elements 280 of anchor frame 201. Radiopaque markers 470 similar or identical to those described in connection with anchor frame 201 may also be included with anchor frame 401.

As should be clear from the above description and a comparison of FIGS. 3 and 6, the main difference between anchor frame 201 and anchor frame 401 that anchor frame includes a plurality of support arms 490. Each support arm 490 is preferably formed of a shape memory alloy such as a nickel titanium alloy (including nitinol). However, support arms 490 may be formed of other metals or metal alloys, or biocompatible polymers, instead of nitinol. In the embodiment illustrated in FIGS. 6-7, each support arm 490 has a first end that is coupled (e.g. via sutures or other fasteners) directly to (or formed integrally with) the stent or scaffolding of anchor frame 401, and a second free end that is coupled to either the inflow or outflow end of the valve-receiving member 450. For example, in the illustrated embodiment, each support arm 490 has a free end with an eyelet or aperture formed therein, with the support wire 460 extending through the eyelet or aperture to couple the support-receiving member 450 to the support arm 490. The support arms 490 may be positioned at spaced distances around the inner circumference of the stent or scaffolding of the anchor frame 401, as shown in FIG. 7. While three or more support arms 490 may be preferable, one or two support arms 490 may provide the desired function. In the illustrated embodiment, the support arms 490 are provided in pairs, with one support arm 490 coupled to the inflow end of the valve-retaining member 450 for each support arm 490 coupled to the outflow end of the valve-retaining member 450. However, this one-to-one correspondence is not requires, and in some embodiments, all support arms 490 may be coupled to the inflow end of the valve-retaining member 450, with no support arms 490 coupled to the outflow end of the valve-retaining member 450, or vice versa. In embodiments in which support arms 490 are coupled to both the inflow and outflow ends of the valve-retaining member 450, the support arms 490 may provide an additional function similar to the stiffening or stretching elements 280 of anchor frame 201. If support arms 490 are provided on only the inflow or only the outflow end of the valve-retaining member 450, it may be desirable (but would not be required) to include stiffening elements similar to elements 280 in valve-retaining member 450.

As described above, the anchor frame 401 provides very secure anchoring to the native tricuspid valve annulus, so that the stent or scaffolding of the anchor frame 401 does not shift up or down relative to the tricuspid valve annulus after deployment. As a result, the direct coupling of the support arms 490 between the stent or scaffolding of the anchor frame 401 and the valve-receiving member 450 (e.g. via the support wires 460) prevents or limits any up and down rocking, or side-to-side tilting, of the valve component 300 after deployment within the anchor frame 401 as the heart beats.

In the embodiment shown in FIG. 6, each support arm 490 is shown as having a first end coupled to an area where the central waist portion 403 transitions to the ventricular portion 404. However, this is merely exemplary, and the support arms 490 may be coupled to the atrial portion 402, the ventricular portion 404, the central waist portion 403, or anywhere in between.

Figures 8A, 8B:
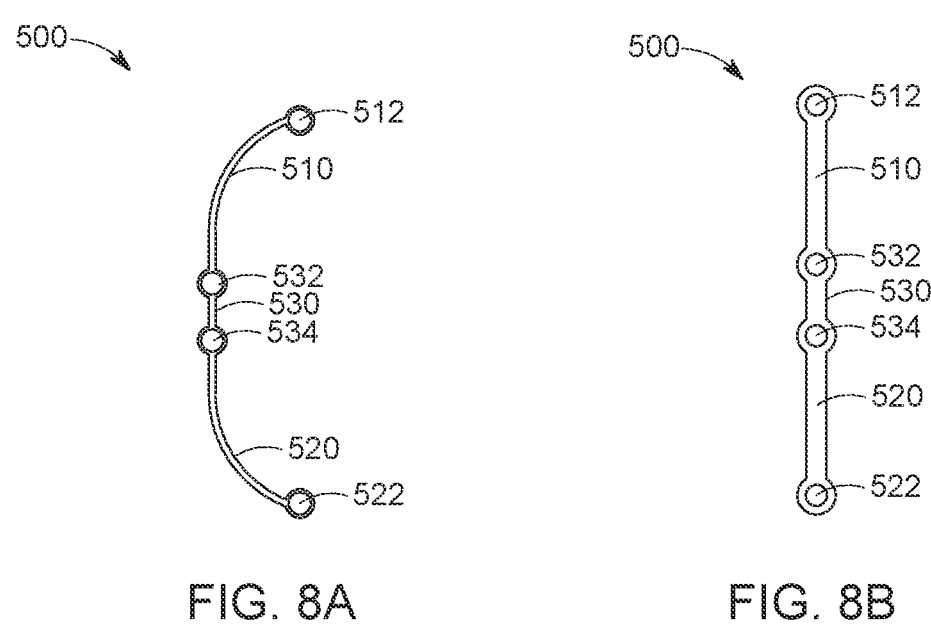
FIGS. 8A-B are side and front views of a support arm for use with an anchor frame.
Figure 8C:
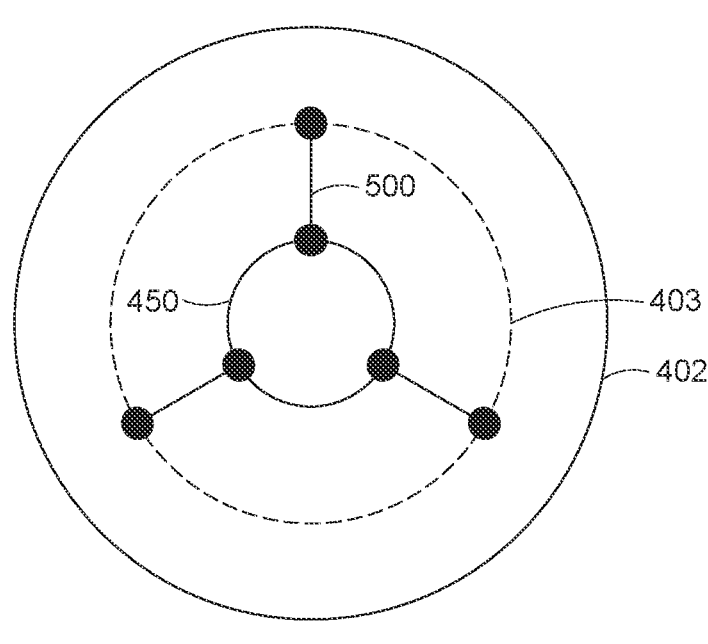
FIG. 8C is a top view of an anchor frame incorporating the support arms of FIGS. 8A-B.
Figure 8D:
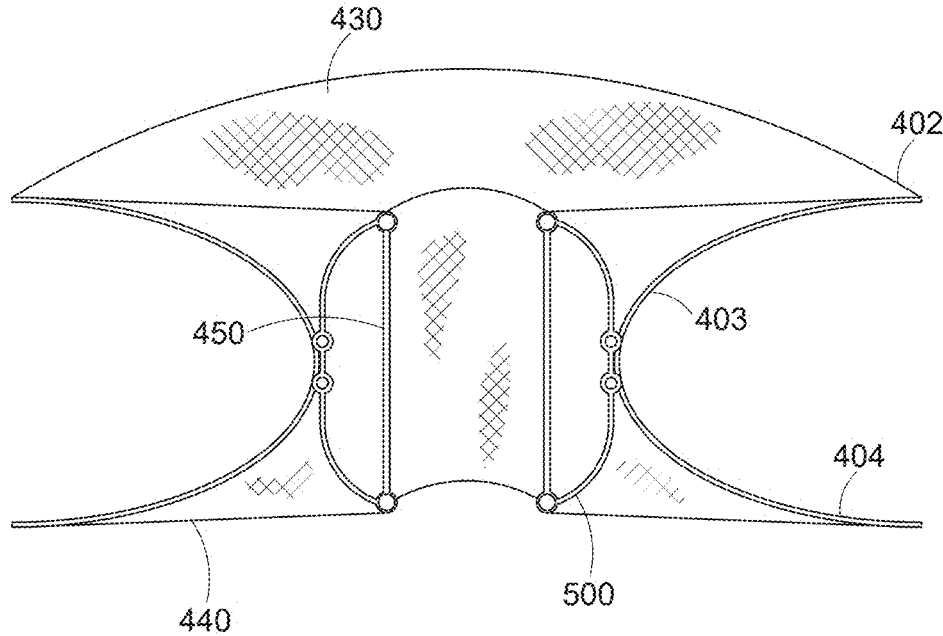
FIG. 8D is a cross-section of the anchor frame of FIG. 8C.

Although the support arms 490 are generally shown as single pieces of metal such as nitinol with eyelets at one end for coupling to a support sife-wire 460, the support arms 490 may have other configurations. For example, FIGS. 8A-B illustrate side and front views of one particular configuration of a support arm 500 that may be used in place of support arms 490. Each support arm 500 may be cut and shaped individually, and may be formed as a single integral member. For example, if the stent of scaffolding of the anchor frame 401 is formed of nitinol, the support arms 500 are preferably formed from nitinol. However, other metals, metal alloys, or polymers may be suitable for use in forming the support arms 500. The support arms 500 may be cut from a flat sheet or component, or cut from a tube, and may be shape set (for example via heat setting) to have a shape similar to that shown in FIG. 8A. For example, each support arm 500 may include an atrial extension 510, a ventricular extension 520, and a central portion 530 between the two. The atrial extension 510 extension and ventricular extension 520 may each have a concave shape with the concavity facing toward the valve-receiving member 450 in the assembled condition, as shown in FIG. 8D. The central portion 530 may have a concave shape with the concavity facing away from the valve-receiving member 450, or otherwise toward the stent or scaffolding of the anchor frame 401. In particular, the central portion 530 may be shape set to have a contour that is complementary to a contour of the central waist 403 where the central portion 530 will attach to the central waist 403. With this configuration, each support arm 500 may form a close fit to the stent of the anchor frame 401 at the points of connection between the two.

Referring generally now to FIGS. 8A-D, a plurality of apertures or eyelets may be formed within the support arm 500 to assist in coupling the support arm 500 to the stent of the anchor frame 401 and the valve-receiving member 450. For example, the atrial extension 510 may include an atrial aperture 512 near a terminal end thereof, and the ventricular extension 520 may include a ventricular aperture 522 near a terminal end thereof. The support wire 460 at the inflow end of the valve-receiving member 450 may be threaded through the atrial aperture 512, and the support wire 460 at the outflow end of the valve-receiving member 450 may be threaded through the ventricular aperture 522, similar to the above description of support arms 490. In other embodiments, the atrial aperture 512 and ventricular aperture 522 may simply be used to suture or otherwise fasten to the valve-receiving component 550, without necessarily threading the support wires 460 through the apertures 512, 522. If the support wires 460 are threaded through the apertures 512, 522, which is the generally preferable method of attachment, the terminal ends of the atrial and ventricular extensions 510, 520 may be twisted relative to the rest of the support arm (e.g. by about 90 degrees) so that the apertures 512, 522 are generally aligned with the circumference of the valve-receiving member 450. In other words, if ends of the extensions 510, 520 are twisted, it may be easier to thread the support wires 460 through the apertures 512, 522.

As best shown in FIGS. 8A and 8D, in the expanded condition of the anchor frame 401, the central portion 530 of the support arm 500 may have a generally complementary profile to the central waisted portion 403 of the stent of scaffolding forming the anchor frame 401. The central portion 530 may include one or more central apertures 532, 534 that have a generally similar configuration to atrial aperture 512 and ventricular aperture 522 (not including any twisting of the apertures). The central apertures 532, 534 may be used to couple the central portion 530 of the support arm 530 to the stent or scaffolding of the anchor frame 401, for example at the central waisted portion 403. Any suitable fasteners, such as sutures, rivets, clips, etc. may be used to couple the central portion 530 of the support arm 530 to the central waisted portion 403.

With each support arm 500 having the central portion 530 directly coupled to the stent or scaffolding of the anchor frame 401, the atrial extension 510 coupled to the inflow end of the valve-receiving member 450 (e.g. via a first support wire 460), and the ventricular extension 520 coupled to the outflow end of the valve-receiving member 450 (e.g. via a second support wire 460), the valve-receiving member 450, and the valve component 300 when received therein, are prevented from up-and-down rocking as the heart beats. Although any number (e.g. 1, 2, 3, 4, 5, 6, etc.) of support arms 500 may be used to stabilize the valve component 300 received within the valve-receiving member 450, as best shown in FIG. 8C, at least three such support arms 500 are preferred, with a preference that the support arms 500 are spaced at substantially equal intervals around the circumference of the central waisted portion 403, although other spacing may be acceptable.

Support arms 500 are just one example of alternative structure to support arms 490. One potential disadvantage of the specific configuration of support arms 500 is that each individual support arm 500 may have a possibility of tilting side to side (e.g. in a direction tangential to the valve-receiving member 450 where the support arms 500 couple to the valve-receiving member 450). Other designs for support arms may be used to achieve different results, including a reduction in the likelihood of such tilting.

Figure 9A:
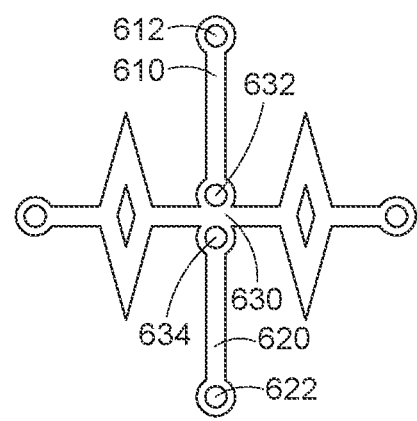
FIG. 9A is a front view of a support arm for use with an anchor frame according to another embodiment of the disclosure, with stabilizers of the support arm being shown in a collapsed condition.
Figure 9B:
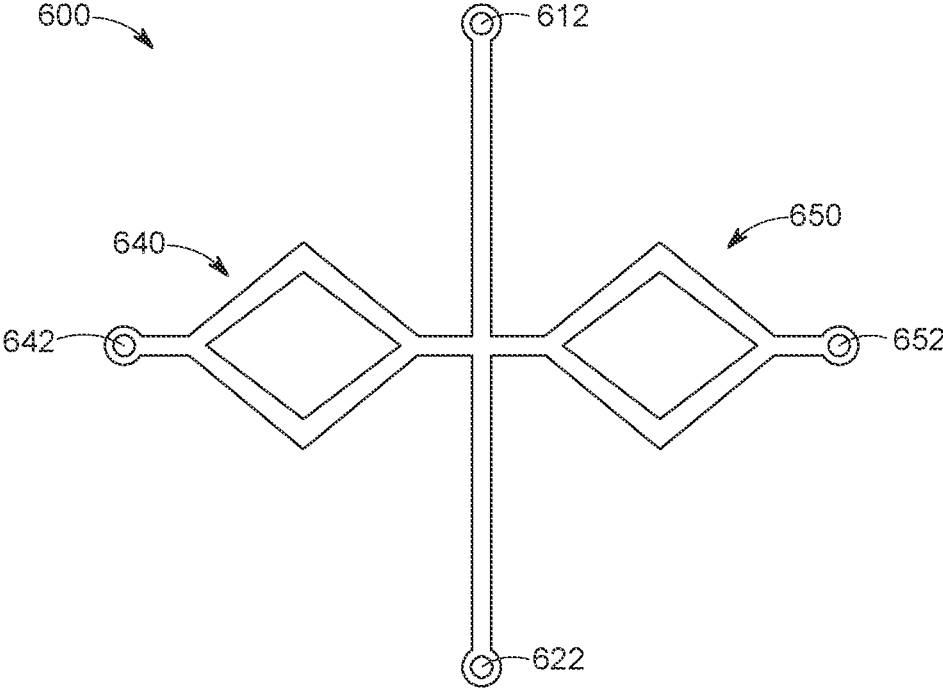
FIG. 9B is a front view of the support arm of FIG. 9A, with stabilizers of the support arm being shown in an expanded condition.

FIGS. 9A-B illustrate another example of a support arm 600 that may be used instead of support arms 500, 490. Support arm 600 may include all of the structure of support arm 500, with additional features. For example, support arm may include an atrial extension with an aperture 612, a ventricular extension 620 with an aperture 622, and a central portion 630 with two apertures 632, 634. In some embodiments, as shown in FIG. 9B, the central apertures 632, 634 may be omitted. All of the disclosure above relative to support arm 500 applies with equal force to support arm 600, and is thus not repeated again here. However, support arm 600 may include additional stabilizing sections. For example, the support arm 600 may include two lateral stabilizers 640, 650 extending from either side of the central portion 630. Each stabilizer 640, 650 may include an expandable and collapsible cell, which may be diamond-shaped, with each cell having a strut that couples to the central portion 630 extending from one lateral apex of the cell, and a strut extending to an aperture 642, 652 coupled to the opposite lateral apex of the cell. The cells of the stabilizers 640, 650 may expand and collapse to drive the apertures away from each other and away from the central portion 630, or toward each other and toward the central portion 630. Preferably, the shape of the cells of each stabilizer 640, 650, which may be diamond-shaped, have a size and shape that generally matches corresponding collapsible and expandable cells of the stent or support structure of the anchor frame 401. For example, if the stent of FIG. 2 were the stent used with anchor frame 401, each cell of each stabilizer 640, 650 may have a shape and size that matches the shape and size of one of the center cells 111c at the waist portion 103. With this configuration, the center apertures 632, 634 (if included) may be coupled (e.g. by sutures or rivets) to the anchor frame 401, with the cells of each stabilizer 640, 650 overlapping correspondingly shaped cells of the stent of the anchor frame 401, and the apertures 642, 652 of the stabilizers coupled to the stent of the anchor frame 401, again for example by sutures or rivets. With this configuration, the stabilizers 640, 650 may provide resistance against tilting at the atrial extension 610 and ventricular extension 620, with the stabilizers 640, 650 being able to expand or collapsed with the stent of the anchor frame 401. It should be understood that, although the various support arms described herein may be separate structures that are attached to the anchor frame, in other embodiments the support arms may be part of the frame structure itself. This is an option for support arms described both above and below.

Figure 9C:
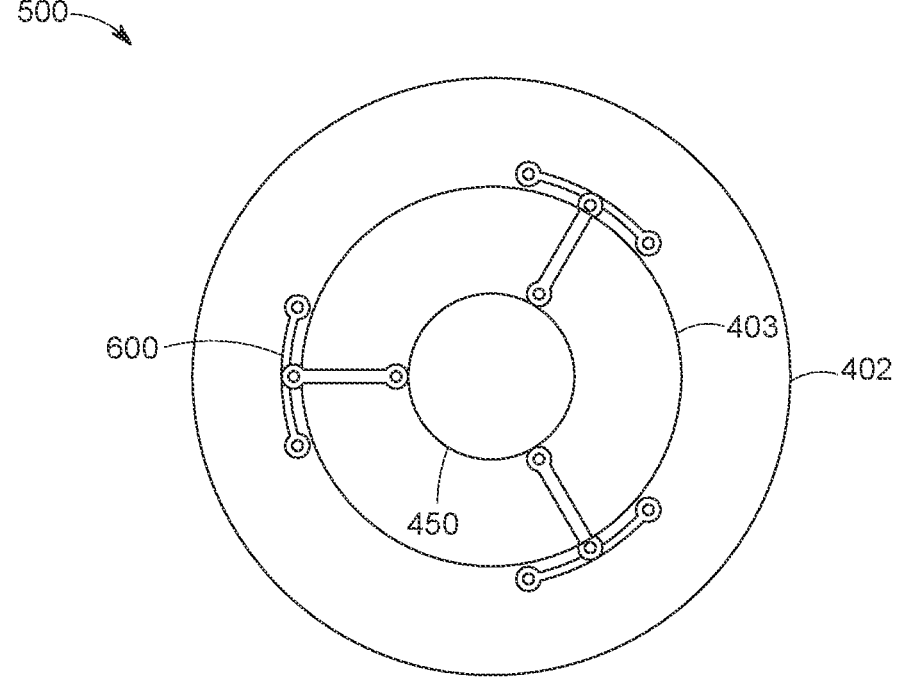
FIG. 9C is a top view of an anchor frame incorporating the support arms of FIGS. 9A-B.

As with support arms 500, any desirable number of support arms 600 may be provided to directly couple the stent of the anchor frame 401 to the valve-receiving member 450, such as 1, 2, 3 (as shown in FIG. 9C), or more. Again, it is preferable, although not required, that the support arms 600 are positioned at substantially equal intervals around the circumference of the stent of the anchor frame 401. As with support arms 500, support arms 600 may be formed of a shape-memory material and cut from a flat sheet or a tube, and then shaped to have the desired contours. The atrial extension 610, ventricular extension 620, and center portion 630 may be shape-set (for example by heat setting) to have similar or identical contours as described in connection with support arm 500. The stabilizers 640, 650 may each be shape-set to the expanded condition (e.g. as shown in FIG. 9B), with a contour that generally follows the circumferential contours of the stent of the anchor frame 401 at or near central portion 403, as shown in FIG. 9C. Each support arm 600 may be positioned with the atrial extension 610 and ventricular extension 620 radially inward of the stent of the anchor frame 401. However, the stabilizers 640, 650 may be positioned either radially inward of, or radially outward of, the stent of the anchor frame 401. For example, if the stabilizers 640, 650 are positioned radially outward of the stent of the anchor frame 401, the atrial extension 610 and ventricular extension 620 may pass through an open cell of the stent of the anchor frame 401 so that atrial and ventricular extensions 610, 620 may couple to the valve-receiving member 450.

FIGS. 10A-B illustrate another embodiment of a support arm 700 that may be used in place of support arms 490, 500, 600. Generally, as shown in FIGS. 10A-B, support arm 700 may be formed as a collapsible and expandable diamond-shaped cell, which may be formed from shape memory material such as nitinol. The support arm 700 may have at one apex an atrial extension 710 defining an aperture 712, and at the opposite apex a ventricular extension 720 defining an aperture 722. As with the atrial and ventricular extensions and apertures of support arms 500, 600, the apertures 712, 722 may be used to couple the support arm 700 to the inflow and outflow ends of valve-receiving member 450, for example to support wires 460. The support arm 700 may include two side struts 630a, 630b extending between the atrial extension 710 and ventricular extension 720, although the side struts 630a, 630b may alternative be thought of two side struts each, to form four struts of a diamond shape. Each of the side struts 630a, 630b, may include one or more apertures defined therein. In the illustrated examples, strut 630a includes two apertures 632a, 634a, and strut 630b includes two apertures 632b, 634b, the apertures being formed at or near the lateral apices of the diamond shape. Although not shown in FIGS. 10A-B, the atrial extension 710 and ventricular extension 720 may be shape set (e.g. via heat setting) to curve or otherwise extend toward the inflow and outflow ends of the valve-receiving portion 450, generally similar to the curvature of support arm 500. The one or more apertures 632a-b, 634a-b may be used to couple the support arm 700 to the stent of the anchor frame 401, in a generally similar fashion as described above for support arms 500, 600.

FIG. 10A illustrates support arm 700 in a partially expanded condition (e.g. not fully collapsed, but not as expanded as shown in FIG. 10B) and FIG. 10B illustrates support arm 700 in an increased expanded condition compared to FIG. 10A. When support arm 700 is coupled to the stent of anchor frame 401, the diamond-shape of the cell preferably generally matches a diamond-shape of a corresponding cell of the stent of the anchor frame 401, although the matching does not need to be perfect. For example, it may be enough that the side struts 630a, 630b, expand and collapse to similar widths as the struts of the stent of the anchor frame 401 to which the side struts 630a, 630b are fastened. As should be clear from FIGS. 10A-B, in a collapsed condition the axial extent (e.g. between the apices defined by the atrial extension 710 and the ventricular extension 720) has a relatively large length L1 compared to the length L2 of the axial extent when in the expanded condition, as shown as FIG. 10B. The circumferential extent (in a direction transverse the axial extent) on the other hand increases from the collapsed condition to the expanded condition. In some examples, the support arms 700 may be cut (e.g., laser cut) from individual sections of material. However, in other examples, the support arms 700 may be cut (e.g., laser cut) from a single tube (e.g., a tube of nitinol). As an example of this, three support arms 700 may be cut from a nitinol tube which has an expanded stage having the same diameter as the waist 403 of the anchor frame 401. IN some embodiments, depending on the shape of the support arms 700, a mid-section of the fabric tube 450 may be formed to slightly narrow in the mid-section to intentionally reduce the flow of blood to through the tube 450. This narrow section, if provided, may be entirely opened when the secondary implant is placed.

The benefits of support arm 700 may include that it is a relatively straightforward design that is easy to manufacture and couple to the stent of the anchor frame 401, and that the connection at two side struts 630a, 630b may help to prevent tilting of the valve-receiving member 450 and the valve component 300 received therein when the heart beats. One potential drawback, however, is that the axial extent decreases upon expansion of the support arm 700. If the valve-receiving member 450 has no capability to change axial lengths, this may present an issue, since the inflow and outflow ends of the valve-receiving member 450 are preferably fixed to the atrial extension 710 and ventricular extension 720. Various modifications to the valve-receiving member 450 to account for this potential drawback are described below.

FIGS. 10C-D illustrate a plurality of support arms 700 coupled to a valve-receiving member 450' that is similar to valve-receiving member 450, with one exception. The remainder of anchor frame 401 is omitted from FIGS. 10C-D, but it should be understood that the support arms 700 would be coupled to the stent of the anchor frame 401, for example at the waisted portion 403, and the various fabrics or sheets described in connection with anchor frame 401 may be included in substantially the same way as described in connection with anchor frame 401. The main difference in valve-receiving member 450' is that it includes an elastic material capable of stretching and returning to an original shape. For example, as shown in FIG. 10C, the support arms 700, when expanded, may be coupled to the inflow and outflow ends of valve-receiving member 450', which may be formed of an elastic material, while the elastic material is in a relaxed state. When the anchor frame 401 is collapsed, and the support arms 700 increase their axial lengths, the valve-receiving member 450' is capable of axially stretching due to its elastic nature. As can be seen, as the support arms 700 collapse, each end of the valve-receiving member 450' may stretch a length of Δx, for a total length change of Δ2x. Once the anchor frame 401 is released from the delivery catheter and deployed into the native tricuspid valve annulus, the arms 700 foreshorten again and the valve-receiving member 450' will "shrink" back to its relaxed state of FIG. 10C.

FIGS. 10E-F illustrate a configuration similar to FIGS. 10C-D, but instead of a valve-receiving member 450' that is elastic, valve-receiving member 450" may be elastic or non-elastic with a plurality of bellows or pleats formed along the length of the valve-receiving member 450". In other words, when in the relaxed expanded condition shown in FIG. 10E, the bellows or pleats may exist in the valve-receiving member 450", for example at spaced apart intervals along the axial extent of the valve-receiving member 450". As the anchor frame 401 collapses and the support arms 700 collapse and increase in axial length, the bellows or pleats unfold to allow the axial length of the valve-receiving member 450" to correspondingly increase. The bellow or pleats may be shape-set so that, as the anchor frame 401 expands again, the bellows or pleats re-form, as shown in FIG. 10E. In some embodiments, valve-receiving member 450' may be formed as a braided material that has a maximum outer diameter. Braids are typically longer when collapsed and shorter when being expanded. Depending on the manufacturing angle of the individual fibers, a braid will expand when a balloon is expanded inside the tube. Expansion will be limited when a further foreshortening of the braided tube is limited, for example by action of the support arms 700. But the valve-receiving member 450" need not be formed of a braid. And, as described in other embodiments above, radial loops (e.g. formed of suture or another support wire) may be provided on the top and/or bottom of the valve-receiving member 450" to prevent the valve-receiving member 450" from opening too much during expansion of the valve within the valve-receiving member 450". It may even be beneficial to have a bulge in the valve-receiving member 450" between top and bottom support wires to hold the prosthetic valve therein or therebetween even more securely. And such support loops or wires may be radiopaque to assist with visualization during delivery.

FIGS. 10G-H illustrate a configuration similar to FIGS. 10E-F, but instead of a valve-receiving member 450" that includes bellows or pleats, valve-receiving member 450''' may be non-elastic with a plurality of folds (e.g. vertical pleats) that are formed when the support arms foreshorten, as shown in FIG. 10G. These folds may be acceptable since the secondary valve (e.g. valve component 300) which will be expanded in the valve-receiving member 450''', sealing at its atrial and ventricular section. Even if some blood enters into the space it will, over time, coagulate and be captured in that defined space.

Although the anchor frames described above, and in particular the valve-receiving members described therewith, have generally been described as intentionally lacking any sort of leaflets or other structure that would function as a temporary valve to bridge the time between the completion of the first stage of implantation and the second stage of implantation, in some embodiments temporary leaflets may be desirable.

For example, FIG. 11 illustrates the anchor frame 401 of FIG. 6, with the exception that anchor frame 401 includes a plurality of prosthetic leaflets 495 coupled to the fabric forming the valve-receiving member 450. Although prosthetic leaflets 495 are shown in the context of the anchor frame 401 of FIG. 6, it should be understood that the prosthetic leaflets 495 may instead be used in the valve-receiving member of any other embodiment disclosed herein, whether or not support arms are included. Rather than being coupled to metal scaffolding or stent structure, which is typical, prosthetic leaflets 495 may be sutured directly to the fabric of the valve-receiving member 450. This may allow the anchor frame 401 to remain small in the collapsed condition (e.g. because additional metal structure is not used to support prosthetic leaflets 495), allowing the anchor frame 401 to be crimped to a small profile, for example 30 French (10 mm) or smaller. However, even if the prosthetic leaflets 495 are sutured directly to the fabric of the valve-receiving member 450, some amount of support structure may be added, for example three individual commissure bars, which may be relatively rigid bars with holes to pass sutures through to suture the prosthetic leaflets 495 to the valve-receiving member 450. As with leaflets 340 of valve component 300, prosthetic leaflets 495 may be formed of bioprosthetic tissues such as pericardial tissue, or synthetic material such as fabrics. Any number of prosthetic leaflets 495 may be provided, but three may be preferable.

The prosthetic leaflets 495 may act as typical prosthetic leaflets, allowing blood to flow in the antegrade direction (toward ventricle portion 404) and restricting blood from flowing in the retrograde direction (toward atrial portion 402). The prosthetic leaflets 495 are shown in the closed or coapted condition in both FIGS. 11-12. The use of anchor frame 401 with prosthetic leaflets 495 may be substantially identical to that described above for the other anchor frames without prosthetic leaflets. The only difference is that prosthetic leaflets 495 provide for valve functionality between the first stage of implantation and the second stage of implantation. Then, when valve component 300 (or a similar valve component) is balloon- or self-expanded into valve-receiving member 450, the temporary prosthetic leaflets 495 are pushed aside, and the prosthetic leaflets 340 of the valve component 300 take over the valve functionality at the tricuspid valve.

It should be understood that the prosthetic leaflets 495 may not be necessary, but may be useful in serving as a bridging function between the first and second stages of implantation, particularly when it is determined that the patient might unduly suffer from an open conduit between the right atrium and the right ventricle for the time between the first and second stages of implantation. Typically, it would be desirable for the prosthetic leaflets 495 to alternate between coapted and being open similar to healthy valve leaflets. However, in some embodiments, the prosthetic leaflets 495 may be modified to intentionally have poor coaptation. As described above, it may be desirable to allow a patient's heart to acclimate to the new hemodynamic conditions after implantation of the anchor frame 401, but prior to implantation of the valve component 300. Although leaving valve-receiving member 450 as an open conduit between the two stages of implantation may provide some time for the heart to acclimate to the new hemodynamics, for some patients the size of that conduit may be too large. But, as noted above, it may also not be desirable to have prosthetic leaflets 495 function normally, as that may result in an effectively instantaneous change in the hemodynamics. Thus, the prosthetic leaflets 495 in some embodiments may be modified to allow for a desired amount of regurgitation while the anchor frame 401 is deployed. With this controlled amount of regurgitation, the heart may have time to acclimate to the new hemodynamics prior to the valve component 300 being deployed within the anchor frame 401, but the regurgitation may not be so large as to remain a significant problem for the patient. Any suitable mechanism may be used to create intentional regurgitation with the temporary leaflets 495. For example, one or more of the temporary leaflets 495 may be pinned open. One way to achieve such pinning is by attaching one or more connectors (e.g. sutures) to the free edge of the one or more temporary leaflets 495, with those sutures also attached to structure of the anchor frame 401, such as the stent portion forming the ventricular disk, support arms, etc. The length of the sutures may be chosen so that the temporary leaflets 495 are restricted from moving far enough to create full coaptation between the temporary leaflets 495. The amount of regurgitation may be fine-tuned based on the length of the sutures, and the number of the temporary leaflets 495 that are coupled to such sutures. If creating intentional regurgitation, it may be desirable for all of the temporary leaflets 495 to be limited via sutures or other connectors, as the sutures or connectors may also prevent inversion of the leaflets (e.g. similar to the function of chordae tendineae). In some embodiments, permanent leaflets may be provided instead of temporary leaflets. More detailed examples of permanent leaflets are described in U.S. Provisional Patent Application No. 63/376,496, titled "Prosthetic Tricuspid Heart Valve," and filed Sep. 21, 2022, the disclosure of which is hereby incorporated by reference herein.

It should be understood that, although embodiments described above include both atrial sheets/fabrics and ventricular sheets/fabrics to suspend the valve-receiving member within the outer anchor, in some embodiments one of those sheets/fabrics may be omitted. In such instances, it would be preferable to provide support to the valve-receiving member via other mechanisms, such as support arms, including any of the embodiments described herein.

According to one aspect of the disclosure, a prosthetic heart valve system is for replacing a native right atrioventricular valve, and the system comprises:

- a collapsible and expandable anchor frame including:
  - a support structure that, in an expanded condition, has a waisted central portion, and atrial and ventricular portions each flared radially outwardly from the central portion, the atrial and ventricular portions sized to clamp an annulus of the right atrioventricular valve therebetween;
  - an atrial sheet coupled to the atrial portion of the support structure and extending radially inwardly to a central aperture in the atrial sheet;
  - a ventricular sheet coupled to the ventricular portion of the support structure and extending radially inwardly to a central aperture in the ventricular sheet; and
  - a valve-receiving member formed of fabric and being generally cylindrical, an inflow end of the valve-receiving member coupled to the atrial sheet and an outflow end of the valve-receiving member coupled to the ventricular sheet to provide a conduit from the central aperture in the atrial sheet to the central aperture in the ventricular sheet through the valve-receiving member; and
- a collapsible and expandable prosthetic heart valve including a stent and a plurality of prosthetic leaflets, the prosthetic heart valve configured to be expanded into and received within the valve-receiving member of the anchor frame; and/or
- one of the atrial sheet and the ventricular sheet is formed of a porous fabric and the other of the atrial sheet and ventricular sheet is formed of a substantially fluid-impermeable fabric; and/or
- at least one radiopaque marker coupled to the valve-receiving member at the inflow end of the valve-receiving member or the outflow end of the valve-receiving member; and/or
- a stretching member coupled to the valve-receiving member, the stretching member being a rigid material extending in a longitudinal direction of the valve-receiving member, the rigid material configured to reduce slack in the valve-receiving member when the support structure of the anchor frame is in the expanded condition; and/or
- a support wire coupled to the valve-receiving member and extending along a circumference of the valve-receiving member; and/or
- the support wire is formed of metal cable; and/or
- the support wire is formed of a suture; and/or
- the support wire includes a first support wire at the inflow end of the valve-receiving member and a second support wire at the outflow end of the valve-receiving member; and/or
- a support arm having a first end coupled directly to the support structure of the anchor frame, and a second end coupled directly to the valve-receiving member; and/or
- the support arm is formed of nickel titanium alloy; and/or
- the support arm includes an atrial extension coupled to the inflow end of the valve-receiving member, and a ventricular extension coupled to the outflow end of the valve-receiving member, a central portion of the support arm being directly coupled to the central portion of the support structure of the anchor frame; and/or
- the atrial extension includes an aperture therein, and the ventricular extension includes an aperture therein; and/or
- a first support wire coupled to the valve-receiving member at the inflow end of the valve-receiving member and extending along a circumference of the valve-receiving member, and a second support wire coupled to the valve-receiving member at the outflow end of the valve-receiving member and extending along a circumference of the valve-receiving member, the first support wire passing through the aperture in the atrial extension of the support arm, and the second support wire passing through the aperture in the ventricular extension of the support arm; and/or
- the support arm includes a first lateral stabilizer and a second lateral stabilizer, the first and second lateral stabilizers extending in opposite directions on opposite sides of the central portion of the support arm; and/or
- the first and second lateral stabilizers each includes an expandable cell that can expand and collapse to move the corresponding lateral stabilizer toward or away from the central portion of the support arm; and/or
- the support arm is a diamond-shaped structure, the central portion including two side struts that each coupled the atrial extension to the ventricular extension; and/or
- the fabric forming the valve-receiving member is elastic; and/or
- the fabric forming the valve-receiving member is inelastic, and includes a plurality of folds or pleats that can unfold to increase an axial length of the valve-receiving member as the support structure of the anchor frame transitions from the expanded condition to a collapsed condition; and/or
- the anchor frame is devoid of any temporary prosthetic heart valve leaflets within the valve-receiving member; and/or
- the anchor frame includes a plurality of temporary prosthetic heart valve leaflets within the valve-receiving member.

According to another aspect of the disclosure, a method is disclosed for replacing a native right atrioventricular valve of a patient, the method comprising:

- delivering a collapsible and expandable anchor frame to the native right atrioventricular valve while the anchor frame is in a collapsed condition within a first delivery sheath;
- deploying the anchor frame from the delivery sheath, and expanding the anchor frame within the native right atrioventricular valve so that an annulus of the native right atrioventricular valve is clamped between an atrial portion of the anchor frame and a ventricular portion of the anchor frame;

after deploying the anchor frame, allowing blood to flow through a conduit of the anchor frame, the conduit formed by a fabric valve-receiving member that has an inflow end and an outflow end, the inflow end of the valve-receiving member being coupled to an atrial sheet that is coupled to the atrial portion of the anchor frame, the outflow end of the valve-receiving member being coupled to a ventricular sheet that is coupled to the ventricular portion of the anchor frame; and after allowing blood to flow through the conduit of the anchor frame, delivering a collapsible and expandable prosthetic heart valve to the anchor frame, and causing the prosthetic heart valve to expand into contact with the valve-receiving member, the valve-receiving member maintaining the prosthetic heart valve within the native right atrioventricular valve; and/or the valve-receiving member is devoid of any temporary prosthetic valve leaflets; and/or expanding the prosthetic heart valve into contact with the valve-receiving member is performed at least two minutes after deploying the anchor frame, such that blood is allowed to flow through the conduit of the anchor frame for at least two minutes; and/or expanding the prosthetic heart valve into contact with the valve-receiving member is performed at least one day after deploying the anchor frame, such that blood is allowed to flow through the conduit of the anchor frame for at least one day; and/or expanding the prosthetic heart valve into contact with the valve-receiving member is performed at least one week after deploying the anchor frame, such that blood is allowed to flow through the conduit of the anchor frame for at least one week; and/or the valve-receiving member includes a plurality of temporary prosthetic leaflets coupled to the valve-receiving member; and/or the temporary prosthetic leaflets are designed to allow regurgitation of blood from the outflow end of the conduit to the inflow end of the conduit; and/or expanding the prosthetic heart valve into contact with the valve-receiving member is performed at least two minutes after deploying the anchor frame, such that regurgitation of blood through the temporary prosthetic leaflets allowed for at least two minutes; and/or expanding the prosthetic heart valve into contact with the valve-receiving member is performed at least one day after deploying the anchor frame, such that regurgitation of blood through the temporary prosthetic leaflets allowed for at least one day; and/or expanding the prosthetic heart valve into contact with the valve-receiving member is performed at least one week after deploying the anchor frame, such that regurgitation of blood through the temporary prosthetic leaflets allowed for at least one week.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A prosthetic heart valve system for replacing a native right atrioventricular valve, the system comprising:
   a collapsible and expandable anchor frame
   that, in an expanded condition, has a waisted central portion, and atrial and ventricular portions each flared radially outwardly from the central portion, the atrial and ventricular portions sized to clamp an annulus of the right atrioventricular valve therebetween;
   an atrial sheet coupled to the atrial portion of the anchor frame and extending radially inwardly to a central aperture in the atrial sheet;
   a ventricular sheet coupled to the ventricular portion of the anchor frame and extending radially inwardly to a central aperture in the ventricular sheet; and
   a valve-receiving member formed of fabric and being cylindrical, an inflow end of the valve-receiving member coupled to the atrial sheet and an outflow end of the valve-receiving member coupled to the ventricular sheet to provide a conduit from the central aperture in the atrial sheet to the central aperture in the ventricular sheet through the valve-receiving member; and
   a collapsible and expandable prosthetic heart valve including a stent and a plurality of prosthetic leaflets, the prosthetic heart valve configured to be expanded into and received within the valve-receiving member.

2. The prosthetic heart valve system of claim 1, wherein one of the atrial sheet and the ventricular sheet is formed of a porous fabric and the other of the atrial sheet and ventricular sheet is formed of a substantially fluid-impermeable fabric.

3. The prosthetic heart valve system of claim 1, further comprising at least one radiopaque marker coupled to the valve-receiving member at the inflow end of the valve-receiving member or the outflow end of the valve-receiving member.

4. The prosthetic heart valve system of claim 1, further comprising a stretching member coupled to the valve-receiving member, the stretching member being a rigid material extending in a longitudinal direction of the valve-receiving member, the rigid material configured to reduce slack in the valve-receiving member when the anchor frame is in the expanded condition.

5. The prosthetic heart valve system of claim 1, further comprising a support wire coupled to the valve-receiving member and extending along a circumference of the valve-receiving member.

6. The prosthetic heart valve system of claim 5, wherein the support wire is formed of metal cable.

7. The prosthetic heart valve system of claim 5, wherein the support wire is formed of a suture.

8. The prosthetic heart valve system of claim 5, wherein the support wire includes a first support wire at the inflow end of the valve-receiving member and a second support wire at the outflow end of the valve-receiving member.

9. The prosthetic heart valve system of claim 1, further comprising a support arm having a first end coupled directly to the anchor frame, and a second end coupled directly to the valve-receiving member.

10. The prosthetic heart valve system of claim 9, wherein the support arm is formed of nickel titanium alloy.

11. The prosthetic heart valve system of claim 9, wherein the support arm includes an atrial extension coupled to the inflow end of the valve-receiving member, and a ventricular extension coupled to the outflow end of the valve-receiving member, a central portion of the support arm being directly coupled to the central portion of the anchor frame.

12. The prosthetic heart valve system of claim 11, wherein the atrial extension includes an aperture therein, and the ventricular extension includes an aperture therein.

13. The prosthetic heart valve system of claim 12, further comprising a first support wire coupled to the valve-receiving member at the inflow end of the valve-receiving member and extending along a circumference of the valve-receiving member, and a second support wire coupled to the valve-receiving member at the outflow end of the valve-receiving member and extending along a circumference of the valve-receiving member, the first support wire passing through the aperture in the atrial extension of the support arm, and the second support wire passing through the aperture in the ventricular extension of the support arm.

14. The prosthetic heart valve system of claim 11, wherein the support arm includes a first lateral stabilizer and a second lateral stabilizer, the first and second lateral stabilizers extending in opposite directions on opposite sides of the central portion of the support arm.

15. The prosthetic heart valve system of claim 14, wherein the first and second lateral stabilizers each includes an expandable cell that can expand and collapse to move the corresponding lateral stabilizer toward or away from the central portion of the support arm.

16. The prosthetic heart system of claim 11, wherein the support arm is a diamond-shaped structure, the central portion including two side struts that each coupled the atrial extension to the ventricular extension.

17. The prosthetic heart valve system of claim 11, wherein the fabric forming the valve-receiving member is elastic.

18. The prosthetic heart valve system of claim 11, wherein the fabric forming the valve-receiving member is inelastic, and includes a plurality of folds or pleats that can unfold to increase an axial length of the valve-receiving member as the anchor frame transitions from the expanded condition to a collapsed condition.

19. The prosthetic heart valve system of claim 1, wherein the anchor frame is devoid of any temporary prosthetic heart valve leaflets within the valve-receiving member.

20. The prosthetic heart valve system of claim 1, wherein the anchor frame includes a plurality of temporary prosthetic heart valve leaflets within the valve-receiving member.

* * * * *